United States Patent
Zhang et al.

(10) Patent No.: US 7,729,867 B2
(45) Date of Patent: Jun. 1, 2010

(54) METHOD FOR INTRODUCING CONJUGATED CAPS ONTO MOLECULAR FRAGMENTS AND SYSTEMS AND METHODS FOR USING THE SAME TO DETERMINE INTER-MOLECULAR INTERACTION ENERGIES

(75) Inventors: John Zeng Hui Zhang, New York, NY (US); Da Wei Zhang, Elmhurst, NY (US)

(73) Assignee: New York University, New York, NY (US)

( * ) Notice: Subject to any disclaimer, the term of this patent is extended or adjusted under 35 U.S.C. 154(b) by 836 days.

(21) Appl. No.: 10/825,186

(22) Filed: Apr. 16, 2004

(65) Prior Publication Data

US 2005/0059039 A1    Mar. 17, 2005

Related U.S. Application Data

(60) Provisional application No. 60/463,753, filed on Apr. 17, 2003.

(51) Int. Cl.
    *G01N 33/00*    (2006.01)
(52) U.S. Cl. .............................. 702/22; 702/19; 702/30
(58) Field of Classification Search .................. None
    See application file for complete search history.

(56) References Cited

OTHER PUBLICATIONS

Merriam-Webster Dictionary, definition of "conjugate." Printed from http://m-w.com/cgi-bin/dictionary. Mar. 18, 2007.*
Ante et al. (Journal of Physical Chemistry A, vol. 103, No. 46, p. 9290-9295, 1999).*
Amovilli et al (Journal of Chemical Physics, vol. 117, No. 7, Aug. 15, 2002).*
Shivarati et al (Computer, IEEE, vol. 25, No. 12, p. 32-44, Dec. 1992).*
Novosadov et al. (Journal of Structural Chemistry, vol. 34, No. 1, 27-32, 1993).*
Ewing et al. (Journal of Computer-aided Molecular Design, vol. 15, p. 411-428, 2001).*
Chen et al., "Fractionation of Peptide with Disulfide Bond for Quantum Mechanical Calculation of Interaction Energy with Molecules," *Journal of Chemical Physics* 120(2):839-844 (2004).
Chen et al., "Theoretical Method for Full ab initio Calculation of DNA/RNA-Ligand Interaction Energy," *Journal of Chemical Physics* 120(24):11386-11391 (2004).
Gao et al., "An Efficient Linear Scaling Method for ab initio Calculation of Electron Density of Proteins," *Chemical Physics Letters* 394:293-297 (2004).
Xiang et al., "Fully Quantum Mechanical Energy Optimization for Protein-Ligand Structure," *Journal of Computational Chemistry* 25(12):1431-1437 (2004).
Zhang et al., "Full ab initio Computation of Protein-Water Interaction Energies," *Journal of Theoretical and Computational Chemistry* 3(1):43-49 (2004).
Zhang et al., "Molecular Caps for Full Quantum Mechanical Computation of Peptide-Water Interaction Energy," *Journal of Computational Chemistry* 24(15):1846-1852 (2003).
Zhang et al., "Molecular Fractionation with Conjugate Caps for Full Quantum Mechanical Calculation of Protein-Molecule Interaction Energy," *Journal of Chemical Physics* 119(7):3599-3605 (2003).
Zhang et al., "New Advance in Computational Chemistry: Full Quantum Mechanical ab Initio Computation of Streptavidin-Biotin Interaction Energy," *J. Phys. Chem.* 107:12039-12041 (2003).
Zhang et al., "Quantum Mechanical Map for Protein-Ligand Binding with Application to β-Trypsin/Benzamidine Complex," *Journal of Chemical Physics* 120(3):1145-1148 (2004).

* cited by examiner

*Primary Examiner*—Karlheinz R Skowronek
(74) *Attorney, Agent, or Firm*—Nixon Peabody LLP

(57) ABSTRACT

A method of introducing conjugated caps onto molecular fragments is described. A first molecule may be decomposed or cut into molecular fragments. Molecular caps may then be introduced in the form of conjugated caps onto the molecular fragments at the decomposition points to form molecular portions. The interaction energy between the molecular portion and a second molecule can then be calculated. This scheme, termed molecular fractionation with conjugated caps, makes it possible and practical to carry out full quantum mechanical (ab initio) calculation of intermolecular interaction energies involving molecules, such as proteins or other biological molecules.

31 Claims, 24 Drawing Sheets

METHOD FOR INTRODUCING CONJUGATED CAPS ONTO MOLECULAR FRAGMENTS AND SYSTEMS AND METHODS FOR USING THE SAME TO DETERMINE INTER-MOLECULAR INTERACTION ENERGIES

This application claims benefit of U.S. Provisional Patent Application Ser. No. 60/463,753, filed Apr. 17, 2003, the disclosure of which is hereby incorporated by reference in its entirety.

FIELD OF THE INVENTION

This invention relates to a method of introducing conjugated caps onto molecule fragments. After the molecule portions have been capped, the intermolecular interaction energy between the decomposed molecule and a second molecule can be calculated using the molecular portions.

BACKGROUND OF THE INVENTION

A grand challenge in computational chemistry and biology is the accurate quantum mechanical calculation of interaction energies for molecules, especially larger biological molecules such as proteins. Due to a larger number of atoms, standard full quantum mechanical or ab initio calculation of intermolecular interaction energy is beyond computational reach. Currently, most theoretical studies of biological molecules employed classical force fields that are built on pairwise atomic interaction potentials. Despite the success of classical force field methods in many applications, they still have significant limitations and quantum mechanical calculations of interaction energies are often required, e.g., in studying enzyme reactions.

Recently, a popular approach to applying quantum mechanical calculation to biological molecules is the hybrid quantum mechanical/molecular mechanical (QM/MM) approach in which one combines quantum mechanical methods with molecular force fields for large molecules. In this hybrid QM/MM approach, one employs quantum mechanical or ab initio methods such as Hartree-Fock (HF) or density functional theory (DFT) methods to treat a small subsystem while using molecular force fields to treat the larger part of the system such as solvent molecules. However, the QM/MM approach cannot provide a proper description of the interface between the QM and MM regions because QM and MM approach are inherently incompatible with each other.

Currently, there are two basic approaches to solving this problem: the link atom approach or its variants and the local self-consistent field (LSCF) method, both of which use strictly localized bond orbitals for the bonds between QM and MM atoms. Despite the progress in these approaches in solving the interface problem, some artifacts still exists in applications of QM/MM methods.

Another approach for calculation of large systems is the linear scaling approach in which the large system is divided into small subsystems and the calculation of the large system is performed for each subsystem individually. The linear scaling approach is based on the local property of the interaction because the effect of energy perturbation in one area is generally localized within its vicinity and decays rapidly going away from it. In this approach, the divide-and-conquer (DAC) and similar methods are commonly employed in theoretical calculations. Although these methods scale linearly with the size of the 2 system, applications are currently limited to calculations using semi-empirical methods for proteins. Ab initio calculations of biological molecules using HF or DFT methods are not feasible.

There is thus a need for developing a practical and efficient full quantum mechanical method for calculating interaction energies of molecules such as proteins. This invention answers that need.

SUMMARY OF THE INVENTION

A first embodiment of this invention relates to a method of introducing conjugated caps onto molecule fragments. In this method, a first molecule is provided. The molecule is then decomposed into two or more molecular fragments. One or more pairs of conjugated caps, which contain a first cap member and a second cap member, are introduced at one or more location in the molecule creating a plurality of molecular portions. Each molecular portion contains a fragment of the first molecule and at least one of the first and second cap members of the conjugated caps. A further embodiment uses the molecular portions to calculate the interaction energy between the first molecule and a second molecule.

A second embodiment of this invention relates to a computer-readable medium having stored instructions for calculating inter-molecular interaction energy between two molecules. The stored instructions comprise instructions for (a) providing a first molecule; (b) decomposing the molecule into two or more molecular fragments; and (c) introducing one or more pairs of conjugated caps having a first member and a second cap member at one or more locations in the molecule to create a plurality of molecular portions. Each molecular portion contains a fragment of the first molecule and at least one of the first and second cap members of the conjugated caps.

A third embodiment of this invention relates to a system for calculating intermolecular interaction energy. The system contains (a) a molecular representation module that provides a first molecule; (b) a molecular decomposing module that decomposes the molecule into two or more molecular fragments; and (c) a molecular cap pair introduction module that introduces one or more pairs of conjugated caps having a first member and a second cap member at one or more locations in the molecule to create a plurality of molecular portions. Each molecular portion in the molecular representation contains a fragment of the first molecule and at least one of the first and second cap members of the conjugated caps.

A fourth embodiment of this invention relates to a composition. The composition contains a molecule having a plurality of units and a plurality of pairs of conjugated caps having a first cap member and a second cap member. Each of the plurality of pairs of conjugated caps is inserted between two of the units under conditions effective to substantially preserve the properties of a chemical bond being cut to insert the pair of conjugated caps. The first cap member substantially mimics the electronic effect of the units of the molecule on a first side of the pair of conjugated caps and the second cap member substantially mimics the electronic effect of the units of the molecule on a second side of the pair of conjugated caps.

DETAILED DESCRIPTION

Figure 3:
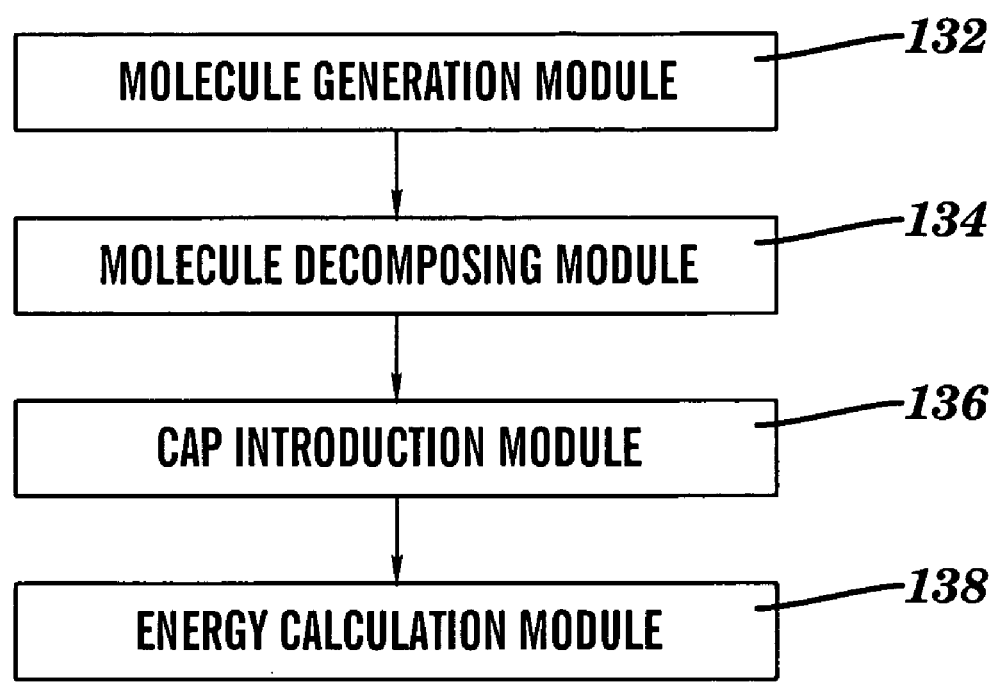
FIG. 3 is a flowchart depicting the method steps of the preferred embodiment.

The first embodiment of this invention relates to a method of introducing conjugated caps onto molecular fragments. A first molecule is provided, and then decomposed into two or more molecular fragments. Pairs of conjugated caps, containing a first cap member and second cap member, are introduced onto the molecular fragments at each decomposition point in the molecule. The pairs of caps are introduced in a manner that, after introduction, each molecular portion contains a molecule fragment and at least one cap member. FIG. 3 is a flowchart depicting the method steps of the preferred embodiment.

When the molecule has been decomposed or cut, the individual pieces of the molecule are referred to as molecular fragments, whereas, after the molecular fragments have been capped, they are referred to as molecular portions.

In the first step, a first molecule is provided. Preferably, the molecule is provided electronically, such as on a computer or other system that has the capability of executing modeling software. Other means capable of providing a molecular, graphical, or mathematical representation of the molecule may also be used. For instance, the molecule may be provided as data plotted on a coordinate system or other structural-information system that describes the molecule. Downloading information off the internet that describes the molecule, such as coordinate data about the molecule, is an example of providing the molecule.

As is well known in the art, there are many different parties providing electronic downloadable information on molecules, such as the protein database bank (pdb). The protein database bank website, as well as other sites, are able to provide the molecule as a set of coordinates, with each atom of the molecule having distinct coordinates. A sample set of x, y, and z coordinates obtained from the protein database bank for protein gb41 is provided below:

| ATOM | 1  | N    | 26.801 | 20.370 | −22.607 |
|------|----|------|--------|--------|---------|
| ATOM | 2  | H1   | 27.720 | 20.763 | −22.465 |
| ATOM | 3  | H2   | 26.112 | 21.023 | −22.263 |
| ATOM | 4  | H3   | 26.740 | 20.022 | −23.553 |
| ATOM | 5  | CA   | 26.672 | 19.167 | −21.736 |
| ATOM | 6  | HA   | 25.835 | 19.339 | −21.059 |
| ATOM | 7  | CB   | 26.403 | 17.903 | −22.573 |
| ATOM | 8  | HB   | 25.490 | 18.038 | −23.152 |
| ATOM | 9  | CG2  | 27.574 | 17.662 | −23.520 |
| ATOM | 10 | 1HG2 | 28.488 | 17.526 | −22.941 |

The coordinates may then be graphically displayed using a plotting program that displays a molecular image of the molecule in a format such as that shown in FIGS. 4A-4C or FIG. 5. Any VRML compliant program or other program, such as Rasmal™, can be used to perform this function. While it is sometimes easier to conceptualize the features of the molecule when it is visually displayed, it is not necessary to display the molecule for the purposes of this invention.

Other software and hardware that has the capability of generating molecules in electronic format or on a computer-readable medium are acceptable. Additionally, other non-electronic means of providing the molecule known to those of skill in the art may also be used; e.g., providing one or more physical models of the molecules.

The first molecule may be selected from any molecule known in the art. Preferably, the first molecule is a polyatomic species. Larger molecules such as materials, proteins, polymers, DNA, or RNA, are typically used as the first molecule because the calculations relating to intermolecular interaction energies are most useful for these types of molecules. However, the first molecule may also be a smaller molecule, such as an ion, a water molecule, an inorganic molecule, an organic molecule, a drug molecule, or a biological molecule.

The first molecule is then decomposed into two or more molecular fragments. The molecule may be decomposed, i.e., cut, by any means known in the art. Preferably, the molecule is decomposed electronically, such as on a computer or via a molecular processing system. When the molecule is provided by means of structural information describing the molecule, the decomposition step may be effected by cutting the molecule into the desired molecular fragments based on the structural description. For instance, if the molecule is represented as a set of coordinates, with each atom of the molecule having distinct coordinates, the molecule can be decomposed by splitting the molecule at the coordinates corresponding to the decomposition points. A set of coordinates may be inputted into the system to designate the decomposition point or a molecular fragment occupying a set of coordinates.

It is also within the capabilities of a skilled artisan to create a software program that decomposes a given molecule when specific decomposition points are provided. Appended to this disclosure is an example of source code of an executable computer program that can be used to decompose a molecule provided by means of a coordinate system. Different programs may be used and may be preferred depending on the hardware a user has at his or her disposal, the mechanism for providing such a program, and other factors determinable through routine experimentation.

Cuts should be made across covalent bonds, preferably across covalent bonds that are single bonds. However, the cuts may be made across all types of bonds, including double and triple bonds. Cuts may also be made across ring structures, such as benzene rings. Since the amount of cuts correspond with amount of desired molecular fragments, a skilled artisan may choose to make many cuts or only a few cuts in the molecule depending on how many molecular fragments is deemed necessary or desirable. The amount of cuts and desired molecular fragments depends on the size of the molecule, the configuration of the molecule, the purpose of the cuts, and other factors that may be determined by routine experimentation by those of skill in the art.

Figure 1:
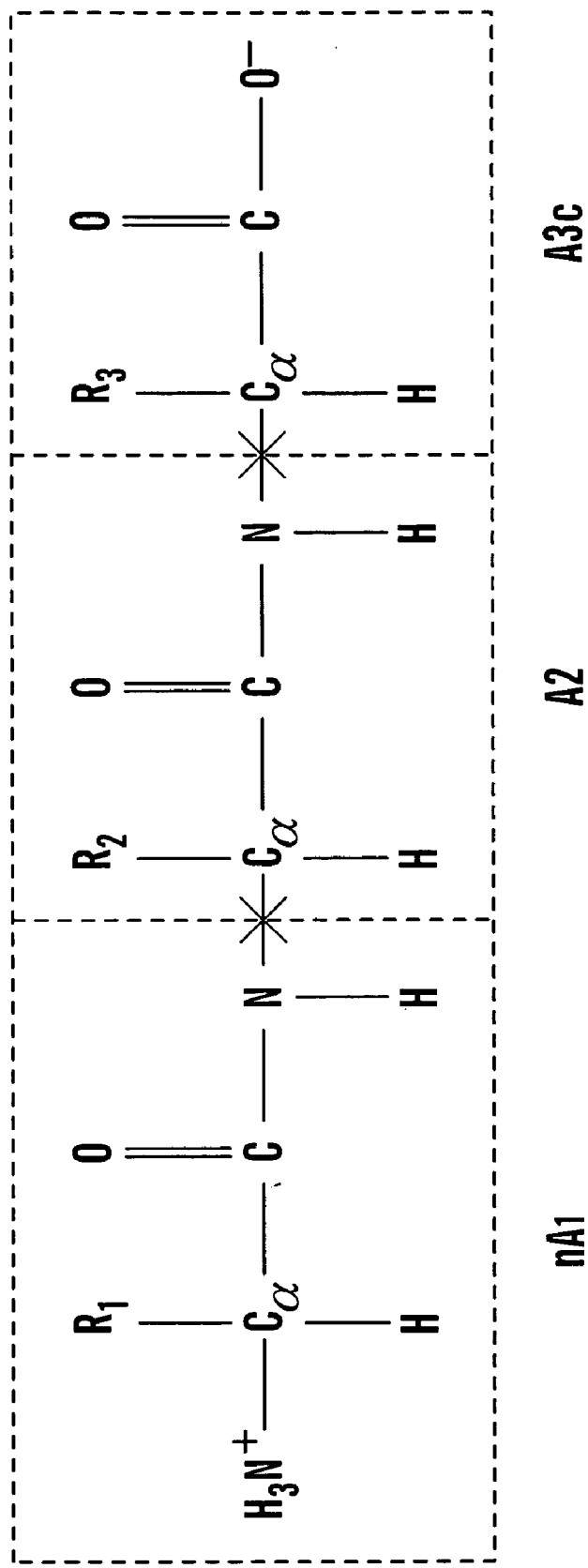
FIG. 1 is a graphical representation of an extended tripeptide and the locations of the cuts where conjugated caps are introduced.

When discussing the decomposition of the molecule, it is useful to look at a theoretical example, such as the decomposition of a protein molecule P with N amino acids. This molecule can be represented at a given (fixed) structure as:

$$P = nA_1-A_2-A_3- \ldots -A_Nc$$

where $A_i$ ($i=1, \ldots, N$) are individual amino acid units, n is the N-terminal of the protein $$n = NH_3^+(NH_2)$$

for the charged (neutral) N-terminal of the protein. The C-terminal of the protein is represented as $$A_Nc = R_N CHCOO^- (R_N CHCOOH)$$

for the charged (neutral) C-terminal. FIG. 1 shows the sequence of a general 3-amino acid peptide (tripeptide) with charged terminals.

As shown in FIG. 1, the cuts could take place between the carbon and nitrogen bonds for the tripeptide, as illustrated in that figure. In this case, the point of the cuts between the carbon and nitrogen represent the decomposition points for that molecule. Of course, cuts do not have to take place across all covalent bonds in the molecule. For instance, the cuts could also be made between the peptide bond for certain advantages or conveniences. As longs as the cuts are made in a manner that a cap may be introduced onto the molecule fragment at the decomposition point, it is not critical where the cuts are made in the molecule or how many cuts are made in the molecule. For larger molecules, many cuts will typically be made, resulting in many molecular fragments. For smaller molecules, only a few, perhaps only a single cut, may be needed.

After the molecule has been cut, at least one pair of caps that are conjugate to each other is introduced at one or more points in the molecule. Caps may be introduced onto the molecular fragment by any means known in the art. Preferably, the caps are introduced by electronically inserting the molecular cap at the decomposition points in the molecule. A molecular processing system may be used to introduce or insert the caps.

For molecules provided by means of structural information describing the molecule, the molecular caps may be introduced based on structural information. If the molecule is represented by a set of coordinates identifying the atoms in the molecule, and decomposed at certain identified decomposition points, molecular caps may be introduced onto each molecular fragment by entering the coordinates of the atoms of the cap member at the desired composition point. The coordinates may then be converted to a visual representation through various modeling programs, such as VRML compliant programs to check the accuracy of the cap introduction.

Each pair of caps contains two cap members, a first cap member and the second cap member. Pairs of conjugate caps are introduced into the molecule at each decomposition point. One cap member is introduced onto each molecule fragment so that the pairs of conjugate caps are aligned adjacent to one another. For illustrative purposes, the caps may be designated $C^i_{ap}$ and $C^{i*}_{ap}$, where i equals 1, ... N. For example, in FIG. 1, cap $C^1_{ap}$ is used to terminate the right end of molecule fragment $nA_1$ at the first decomposition point, while its conjugated cap $C^{1*}_{ap}$ is employed to terminate the left end of molecule fragment $A_2$; similarly, cap $C^2_{ap}$ is employed to terminate the right end of molecule fragment $A_2$ at the second decomposition point, while its conjugate cap $C^{2*}_{ap}$ is used to terminate the left end of molecule fragment $A_3c$.

The caps should be introduced onto the molecule fragments so that each molecular portion will contain the molecule fragment and at least one cap member. In FIG. 1, the left-hand molecule portion contains molecule fragment $nA_1$ and cap member $C^1_{ap}$; the middle molecule portion contains molecule fragment $A_2$ and cap members $C^{1*}_{ap}$ and $C^2_{ap}$; the right-hand molecule portion contains molecule fragment $A_3c$ and cap member $C^{2*}_{ap}$. Thus, the right and left-hand molecule portions contain a molecule fragment and one cap member, while the middle molecule portion contains a molecule fragment and two cap members.

Caps are atoms or radicals that bond with the fragment of the molecule that has been severed at the decomposition point. The caps serve two purposes. First, they preserve the property of the valence bond being cut. The caps should preserve this property as closely as possible, serving a similar purpose as the link-atom in the QM/MM approach discussed above. Second, the caps should mimic as much as possible the effect of the original molecular part being cut away from the remaining fragment. For example, in FIG. 1, $C^1_{ap}$ should closely represent the electronic effect of everything to the right side of the first decomposition point, and $C^{1*}_{ap}$ should closely represent the electronic effect of $nA_1$ on the $A_2$ unit.

One skilled in the art may choose from various possible molecular caps when choosing suitable molecular caps using the criteria described above. This, of course, also applies for molecular caps $C^1_{ap}$ and $C^{1*}_{ap}$. In FIG. 1, the first cap $C^{1*}_{ap}$ could be $NH^+_3$ ($NH_2$) for the charged (neutral) N-terminal. Other caps placed in the middle of the molecule may be, for example $$C^i_{ap} = R_{i+1} C_\alpha H_2$$

for (i=1, ..., N−1). The right-end (C-terminal) cap is simply defined as $$A_N C^N_{ap} = R_N C_\alpha HCOO^- (R_N C_\alpha HCOOH)$$

for the charged (neutral) C-terminal (cf. FIG. 1). The corresponding conjugate caps are then

for (i=1, ..., N−1).

After a molecule has been decomposed and capped with conjugated caps to create a plurality of molecular portions, the molecular portions may be used to measure intermolecular interaction energy. Intermolecular interaction energy calculations attempt to measure the transfer of energy between two given molecules. When calculating intermolecular interaction energy, at least two molecules are provided. In the method of this invention, the second molecule may be any molecule that one wishes to use in comparison to or in reference to the first molecule. Typically, the second molecule is a smaller molecule, such as an ion, a water molecule, an inorganic molecule, an organic molecule, a drug molecule, or a biological molecule. Water is perhaps the most common second molecule used in basic intermolecular-interaction-energy calculations. When calculating intermolecular interaction energies for proteins and peptides, drug molecules and biological molecules represent preferred second molecules because of the practical benefit associated with protein inhibitors in drug discovery. However, any molecule may be used as the second molecule, included those listed as acceptable molecules for the first molecule.

Once the first molecule has been decomposed into molecular fragments having conjugate caps, the intermolecular interaction energy between the first molecule and a second molecule can be calculated. While interaction energies may now be calculated, the use of molecules having molecular portions with conjugated caps is not limited to interaction-energy calculations. For instance, molecules having molecular portions with conjugated caps may also be used for calculations for determining the electron density of the molecules, dipole moment, electrostatic potential, and intra-molecular energy.

In this calculation, the interaction energy is determined between each of the molecular portions in the first molecule and the second molecule. Interaction energy may be calculated using the well known full quantum mechanical or ab initio calculations. However other interaction energy calculations known to those of skill in the art may also be used. Preferably, software or hardware is used to make the calculations. The Gaussian™ software has the capability of performing full quantum mechanical interaction energies. This program may be obtained at Gaussian's website. Each of these interaction energies is then added or summed together to provide a total interaction energy of the molecular portions.

Likewise, the conjugated cap interaction energy may be determined for each pair of conjugated caps and the second molecule. The same interaction energy calculation used for determining the interaction energies of the molecular portions, e.g., the full quantum mechanical or ab initio calculations, should also be used for determining the interaction energies of the conjugated caps. The total interaction energy of the conjugated caps may then be determined by summing together all the conjugated cap interaction energies.

Once the total interaction energy of the molecular portions and the total interaction energy of the conjugated caps have been calculated, the intermolecular interaction energy between the first molecule and the second molecule can be determined by subtracting the total interaction energy of the conjugated caps from the total interaction energy of the molecular portions.

In a preferred embodiment, a molecular interaction energy system is used to sum together the molecular portion and conjugated cap interaction energies and a interaction adjustment system is used to subtract the total interaction energy of the conjugated caps from the total interaction energy of the molecular portions.

The calculation of interaction energies with this process, termed molecular fractionation with conjugate caps (MFCC) method, aims to provide accurate molecular interaction energies for molecules, especially large polyatomic molecules like protein, by means of full quantum mechanical electron structure calculations. By breaking the molecule into individual amino fragments that are properly capped, the interaction energy of a second molecule with the first molecule at a given structure can be obtained by proper combination of the interaction energies between the second molecule and individually capped protein fragments of the first molecule. The extra interactions between the second molecule and the introduced caps are canceled by subtracting the interaction between the molecule and the artificial molecules formed by conjugate caps. The MFCC scheme is particularly suitable for obtaining accurate ab initio interaction energies between a protein with a fixed structure and another molecule. The MFCC scheme is highly efficient for ab initio calculation and scales linearly with the size of the first molecule. In addition, since the interaction energies between the second molecule and individual molecule fragments of the first molecule can be calculated independently, it is particularly suitable for calculation on multi-node computer clusters.

The basic approach of to the calculation interaction energy using MFCC is based on the hypothesis that first-molecule/second-molecule interaction energy is localized. While not wishing to be bound by this theory, it is believed that it is possible to accurately represent the interaction energy between the molecules as a sum over interactions between the second molecule and individual fragments of the first molecule. In this approach, the interaction of the second molecule with the first molecule involving simultaneous multi-fragment interactions are assumed to be negligible.

Computing systems may be utilized to run the interaction energy calculations. Different computing systems or devices may be used for each calculation, or a single computing system may be used to run all the calculations together. It may be preferable to use different computing system or device for each molecular portion. For example, a first computing system may be used to calculate the interaction energy between a first molecular portion and the second molecule, a second computing system may be used to calculate the interaction energy between a second molecular portion and the second molecule, and additional computing systems may be implemented for each additional molecular portion. More than one computing system or device may also be implemented for each portion of the molecule. The calculations may be performed on parallel or multi-processor computers or other systems known in the art.

Figure 2:
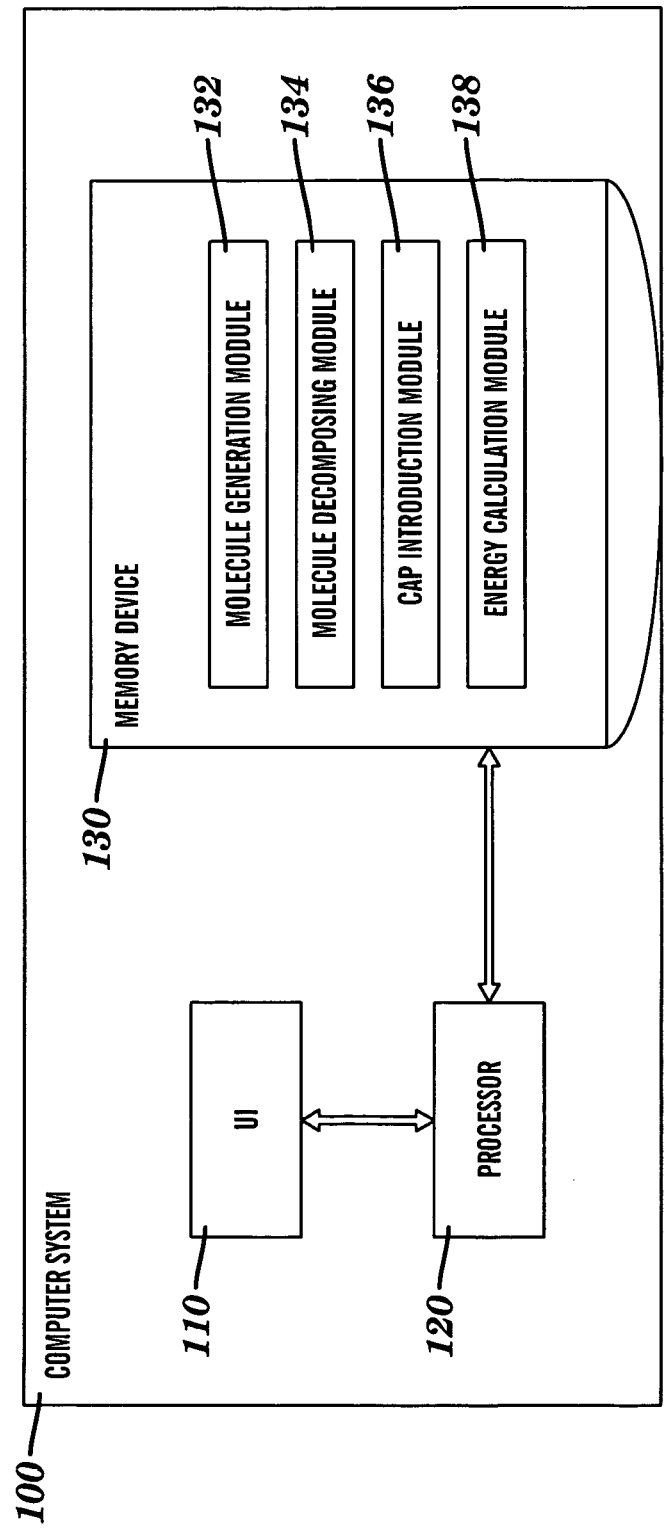
FIG. 2 is a block diagram of a computer system for practicing the method of the preferred embodiment.

FIG. 2 illustrates computer system 100 in accordance with a preferred embodiment that can be used to accomplish the methods of the invention. Computer system 100 can include a variety of devices and can be embodied in a personal computer, workstation, or the like. The various devices can be coupled in any manner, such as over a LAN, WAN, or through other channels. Computer system 100 includes user interface (UI) 100 which serves to provide all communications and interactions between computer system 100 and a user in a known manner. UI 100 can include a display and a keyboard or other input device. Further, UI 100 can include any necessary software and/or hardware interfaces for effecting the interface between the user and system 100 in a known manner. For example, UI 100 can include software to implement the standard WINDOWS™ user interface.

Computer system 100 also includes processor 120, which can be any type of known processor, such as a PENTIUM IV™, POWERPC™, or other processor. Processor 120 executes instructions stored as software code in memory device 130 and/or other memory devices. Memory device 130 includes a computer readable media, such as a hard disk, a CD, a DVD, a floppy disk, or any other type of media for storing computer readable instructions. Instructions are read from memory device 130 in a known manner to execute the instructions on processor 120. Of course, there can be other instructions, such as an operating system or the like, to facilitate execution of instructions stored on memory device 130. Also, memory device 130 can be constituted of plural devices or a single device.

Memory device 130 includes molecule generation module 132 which provides instructions for selecting/generating, i.e., providing, a molecule in the manner described above. For example, molecule generation module 132 can include known electronic downloadable databases, such as the protein database bank. Memory 130 also includes molecule decomposing module 134 for accomplishing the decomposing step described above. Molecule decomposing module 134 can also include program code designed to decompose molecules, such as the program code appended to this disclosure. Similarly, cap introduction module 136 includes instructions for accomplishing the cap introduction step described above. This also can be accomplished using the same or different program code designed to decompose the molecule. Finally, energy calculation module 138 includes instructions for calculating the intermolecular interaction energy as described above. The programming steps required for accomplishing energy calculation module 138 are well within the ability of a skilled programmer in light of the functional disclosure provided herein. Energy calculation module 138 can include energy calculation software such as the programs produced by Gaussian™.

The second embodiment of this invention relates to a computer-readable medium, such as the medium of storage device 130, having stored instructions for calculating the intermolecular interaction energy between two molecules. When the instructions are executed by at least one processor, the execution causes the processor to perform the steps of (a) providing a first molecule; (b) decomposing the molecule into two or more molecular fragments; and (c) introducing one or more pairs of conjugated caps having a first member and a second cap member at one or more locations in the molecule to create a plurality of molecular portions. Each molecular portion contains a fragment of the first molecule and at least one of the first and second cap members of the conjugated caps.

The computer-readable medium may also include instructions for calculating the intermolecular interaction energy between the first molecule and a second molecule. The processor may perform this function in addition to the functions described above during the same execution. The calculation of the interaction energy is the same as that described above in the first embodiment of the invention.

The third embodiment of this invention relates to a system for calculating intermolecular interaction energy. The system contains (a) a molecular representation module that provides a first molecule; (b) a molecular decomposing module that decomposes the molecule into two or more molecular fragments; and (c) a molecular processing module that introduces one or more pairs of conjugated caps having a first member and a second cap member at one or more locations in the molecule to create a plurality of molecular portions. Each molecular portion in the molecular representation contains a fragment of the first molecule and at least one of the first and second cap members of the conjugated caps.

The system for calculating intermolecular interaction energy may be a computer system. However, other systems that would perform similar functions are envisioned. A first molecule may be provided in the form a molecular, graphical, or mathematical representation. An example of a mathematical representation is a molecule defined by a set of coordinates (x, y, z), wherein each atom of the molecule occupies a distinct location in the coordinates. Molecular processing systems or modules perform the other functions of decomposing the molecule, introducing conjugate caps onto the molecule fragments, and determining or calculating the interaction energies. Utilizing molecular, graphical, or mathematical representations and molecular processing modules allows for the process to be performed electronically, which is the preferred means of execution.

A fourth embodiment of this invention relates to a composition. The composition contains a molecule having a plurality of units, and a plurality of pairs of conjugated caps having a first cap member and a second cap member, wherein each of the plurality of pairs of conjugated caps has been inserted between two of the units under conditions effective to substantially preserve the properties of a chemical bond being cut to insert the pair of conjugated caps. The first cap member substantially mimics the electronic effect of the units of the molecule on a first side of the pair of conjugated caps and the second cap member substantially mimics the electronic effect of the units of the molecule on a second side of the pair of conjugated caps. The function of the cap members is discussed above in the disclosure relating to the selection of the cap members.

The composition may be formed by the methods described above, i.e., the molecule may be provided, decomposed, and have conjugated caps introduced onto the molecule fragments. This forms a composition wherein the molecule contains a plurality of units that are separate from one another.

Alternatively, the pairs of conjugated caps may be fused or otherwise linked to one another to attach the molecular portions to one another in forming the composition. Since each cap member is a radical that lies adjacent to its conjugate, the conjugate cap members may fuse or form with each other through processes well known in the art. When the units are fused or linked together, the molecule can become a single continuous composition.

While each of the four embodiments described above may be used to determine the intermolecular interaction energy between two molecules, the steps of providing a molecule, decomposing the molecule, and introducing conjugated caps onto the molecule fragments may also be used to determine electron density, dipole moment, electrostatic potential, and other calculations. The determination of the electron density p, dipole moment d, and electrostatic potential Φ follows essentially the same method steps as that for intermolecular energy disclosed above.

Interaction Energy Calculations using a Protein Molecule

This calculation of molecular fractionation with conjugated caps may be expressed abstractly using the protein molecule P with N amino acids example discussed above. Using V(M-P) to denote the interaction energy between the molecule M (the second molecule) and the protein P (the first molecule) with N amino groups, the above fractionation scheme is used to represent V(M-P) by $$V(M-P) = \Sigma V(M - C^{i-1*}_{ap} A_i C^i_{ap}) - \Sigma V(M - C^{i*}_{ap} C^i_{ap}) \quad (1)$$

The first term V $(M-C^{i-1}{}^*_{ap}A_iC^i_{ap})$ in Eq. (1) represents the interaction energy between the molecule M and a capped protein fragment $C^{i-1}{}^*_{ap}A_iC^i_{ap}$ where both ends of the fragments $A_i$ are capped with covalent bonds. The second term in Eq. (1) is the interaction between the molecule M and an artificial molecule formed from conjugate caps $Am_i=C^{i*}_{ap}-C^i_{ap}$. The calculated interaction energies are normalized by subtracting out the values at some asymptotic geometry. The geometries of the cap atoms are kept exactly the same in the calculation of both interaction energies in Eq. (1) to ensure that the artificial interactions between the molecule M and the caps are canceled. The energy given in Eq. (1) describes the proper inter-molecular energy between the protein P with a fixed structure and the molecule M; it does not give the correct internal energy of the protein itself.

Using Eq. (1), the interaction energy between a protein P and a molecule M can be obtained by simple summation over individual interaction energies between the molecule and the capped protein fragments that can be obtained by ab initio calculations such as HF, DFT or even higher level quantum chemistry methods. Obviously, the method scales linearly with the size of the protein. Since the calculation of the individual interaction energy in Eq. (1) is independent of each other, the method can be easily parallelized and is thus especially suitable for quantum calculation of interaction energies between proteins and, for example, drug molecules. However, the interactions between proteins and other molecules may easily be obtained using this method. Additionally, the method may be applied to other materials besides proteins, such as peptides, polymers, DNA, and RNA.

The conjugate caps can then be coupled to form artificial molecular species whose interaction with the external molecule will be calculated to cancel out the artificial molecular interaction with individual caps. Thus the calculation of the original interaction energy between the molecule M and the protein P can be replaced by calculation of interaction energy between molecule M and individual protein fragments. The two protein fragments whose interactions with the molecule need to be calculated are the capped protein fragments having the molecular formula

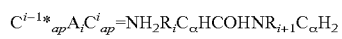

and the coupled caps having the molecular formula

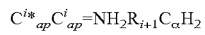

Since these fragments are relatively small molecules, the interaction energy between the M molecule and these small fragments can be calculated by ab initio methods with high efficiency. Since these individual interaction energies are calculated independent of each other, one can easily perform desired ab initio calculations on parallel or multi-processor computers to achieve greater real-time throughput.

The atomic positions of the cap atoms should be exactly the same as that of the cutoff protein parts replaced by the caps. This avoids the possible artifacts due to the placement of atoms in empty space of configuration.

EXAMPLES

The following examples make reference to the figures and results produced in those figures. The following examples and numerical tests are intended to illustrate, not limit, the invention.

Figure 4A:
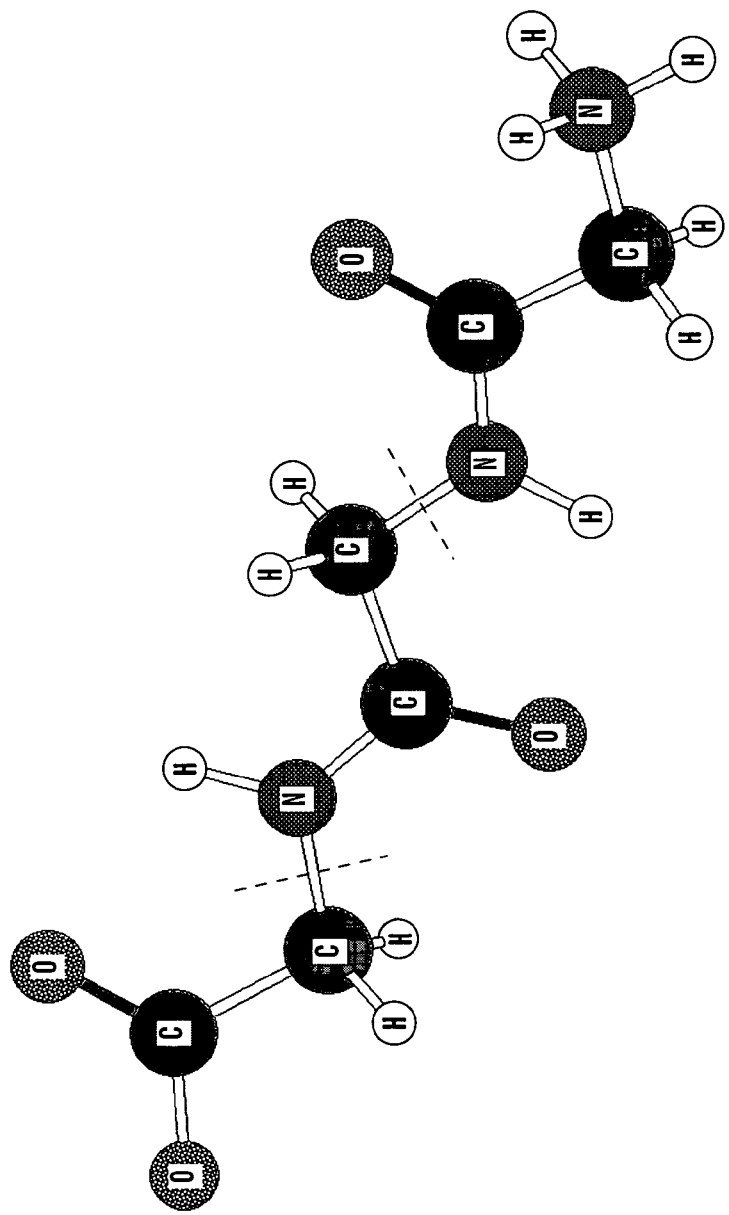
FIGS. 4A-4C represent the all-atom figure of three peptides: (a) Gly-Gly tripeptide; (b) Me-His-Ser-Me dipeptide with both terminals replaced by methyl groups; and (c) Gly-Ser-Ala-Asp-Val pentapeptide.
Figure 4B:
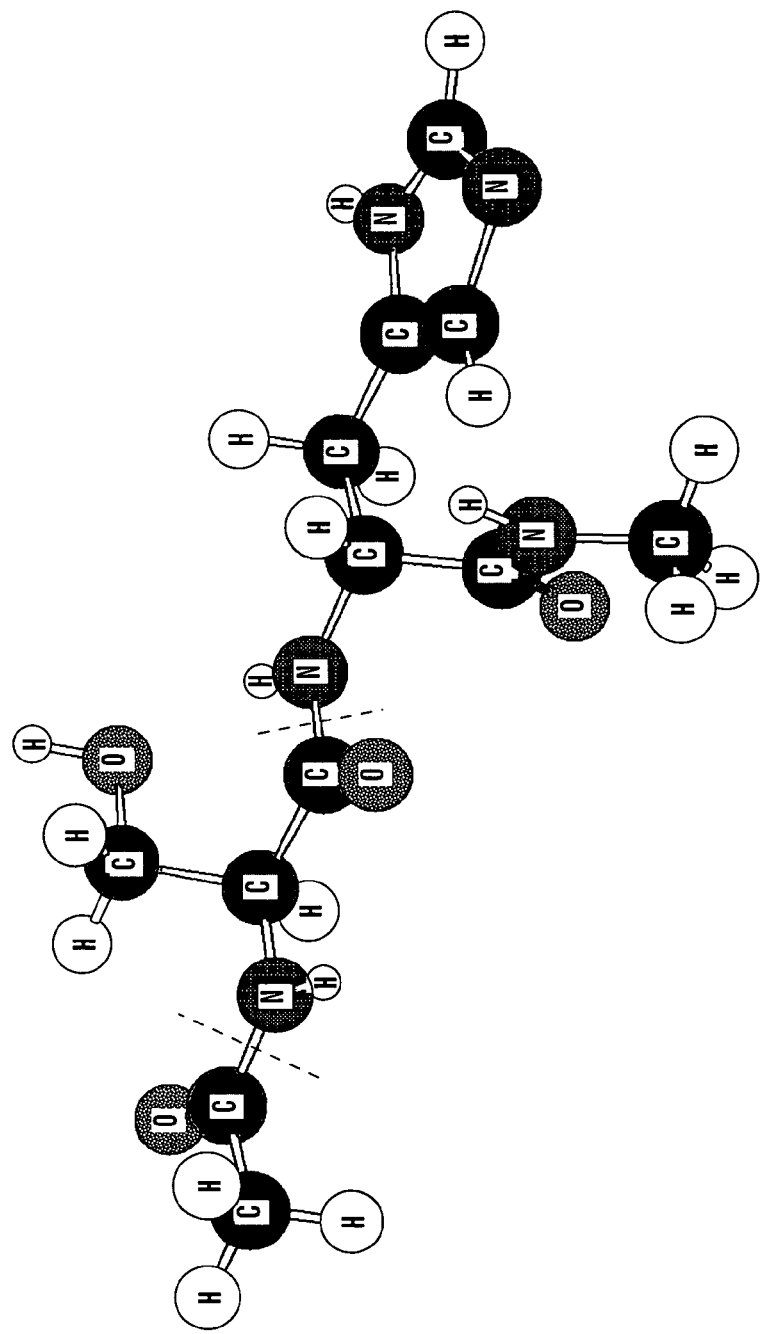
Figure 4C:
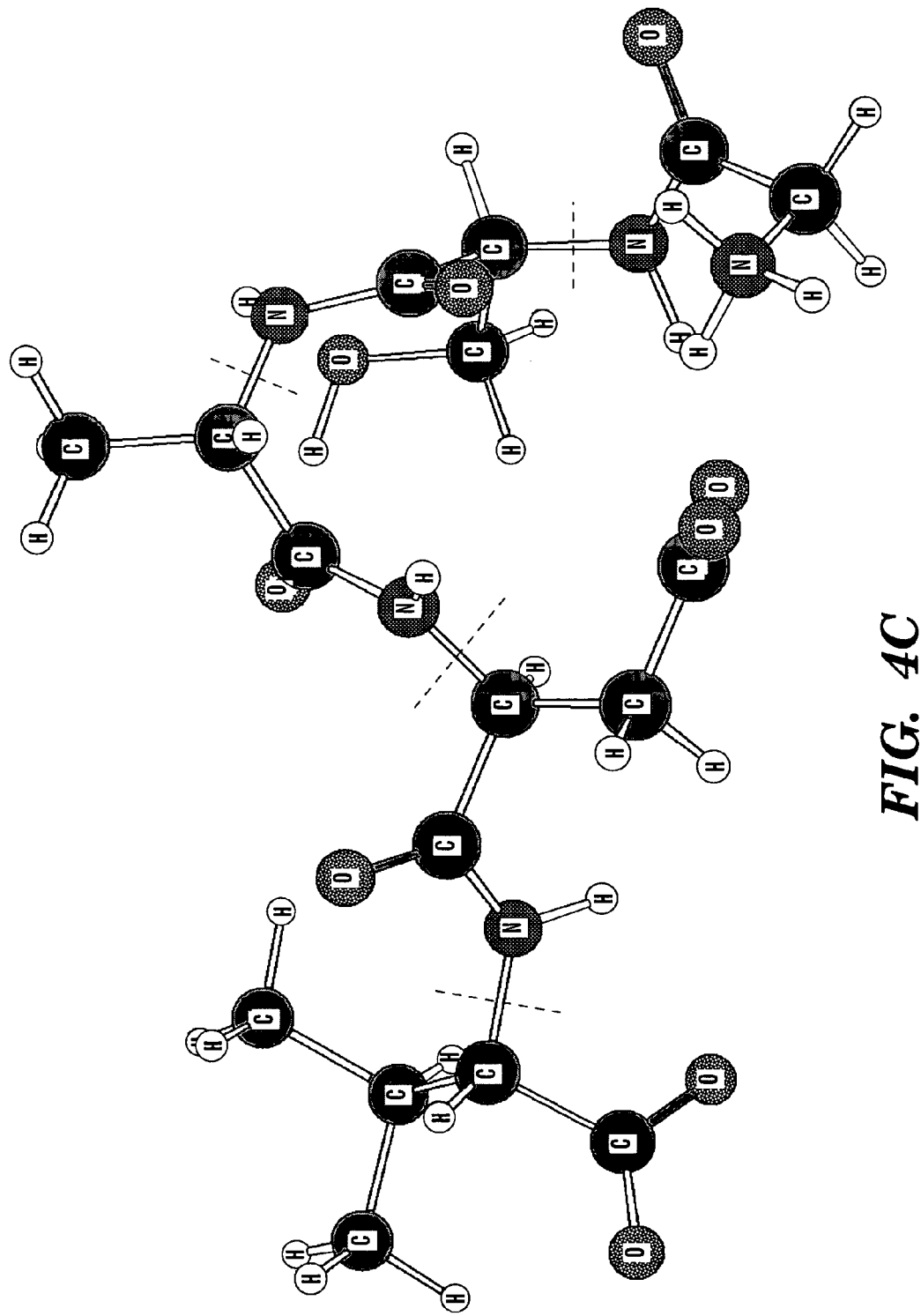

The above approach has been tested on a number of peptides interacting with a water molecule and the results of calculations are compared to the full system (FS) ab initio calculation. Three different peptides were chosen, as shown in FIGS. 4A-C. The first peptide is composed of three glycine (Gly-Gly-Gly) with charged terminals as shown in FIG. 4A. This peptide has a stretched structure whose energy was not optimized. The second peptide is composed of two amino acids but both ends are capped with the methyl group, i.e., Me-His-Ser-Me as shown in FIG. 4B. The structure of this peptide has been optimized using AMBER force field. The third example is a five-base peptide Gly-Ser-Ala-Asp-Val (SEQ ID NO. 1) whose structure has also been optimized using the force field. The interaction energies between these three fixed-structure peptides and a water molecule in gas phase were calculated. The MFCC results were compared with the corresponding full system ab initio calculations. All ab initio calculations were reported using the Gaussian98 package.

Figure 5:
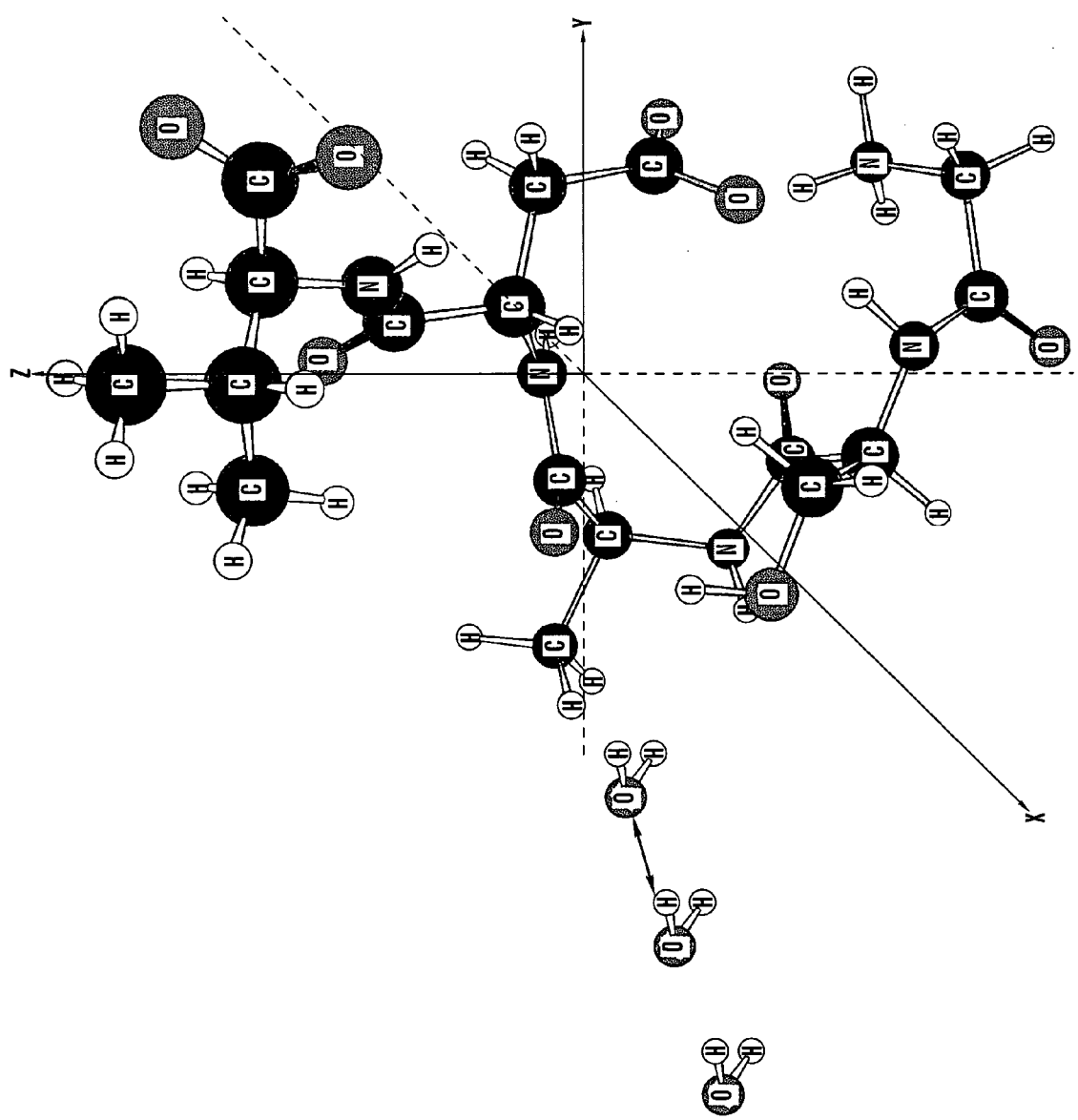
FIG. 5 represents the coordinate system with the origin centered on the center-of-mass of Gly-Ser-Ala-Asp-Val. The interaction potential is calculated for the water molecule approaching the center-of-mass of the peptide from specified spherical angles ($\theta$, $\phi$).

No geometry optimization was done to find minimum energy structures of the peptide/water complex. Instead, different geometries along which the water molecule approaches the peptides were selected. FIG. 5 shows the coordinate system in which the origin of the space-fixed coordinate system is at the center-of-mass of the Gly-Ser-Ala-Asp-Val peptide whose geometry is frozen. The water molecule approaches the center from different spherical angles (θ, φ). Similar coordinate systems are used for the other two peptides. To minimize the number of coordinate changes, the water molecule stays rigid with its orientation shown in FIG. 5. along the potential curve to be calculated.

Figure 6:
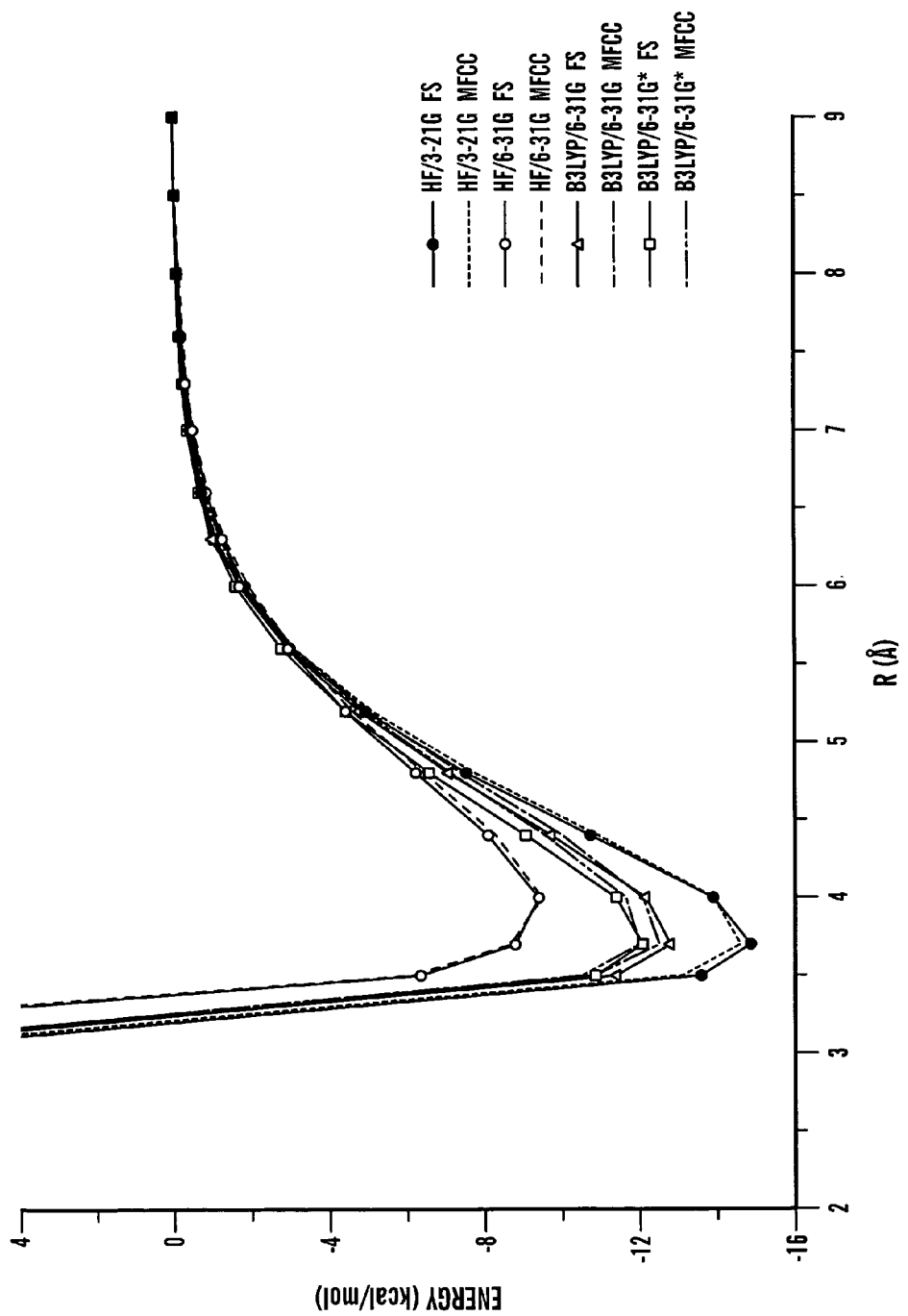
FIG. 6 represents a comparison of ab initio and DFT calculations for triglycine/water interaction potential between the MFCC and FS (full system) calculations using different basis sizes. The approaching spherical angles of water are fixed at (90, 0).
Figure 7B:
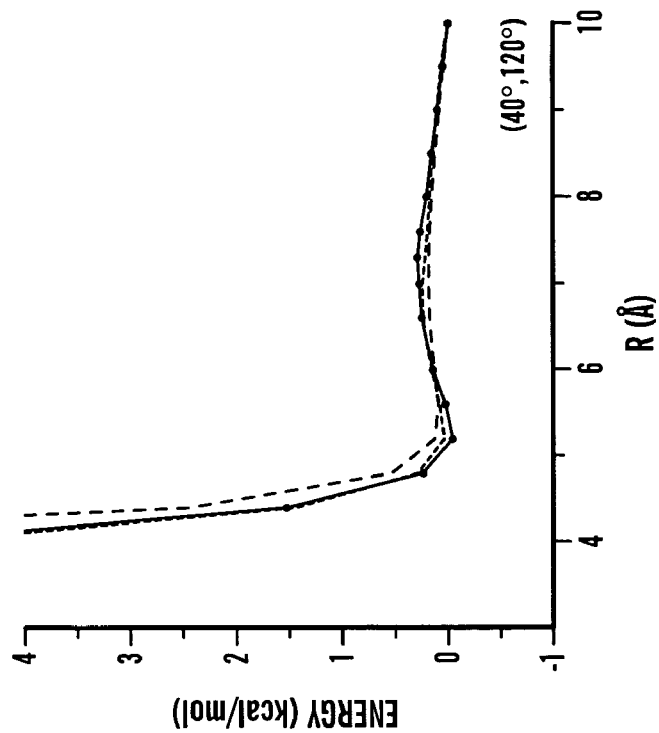
FIGS. 7A-7F represent one-dimensional (1D) potential curves for triglycine/water interaction at various directions obtained by MFCC and FS calculations using DFT B3LYP/6-31G. The solid line with dots are the FS result, dotted lines are MFCC results and dashed lines are the results from AMBER force fields.
Figure 7A:
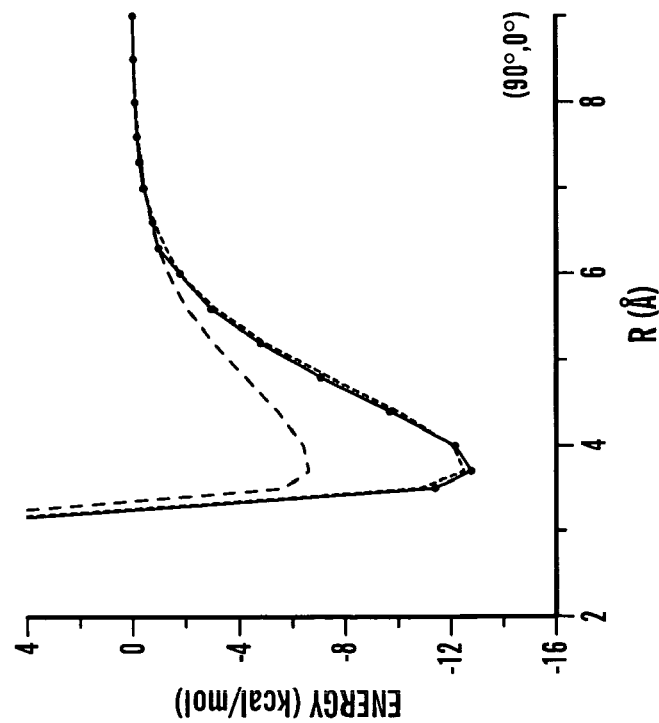
Figure 7D:
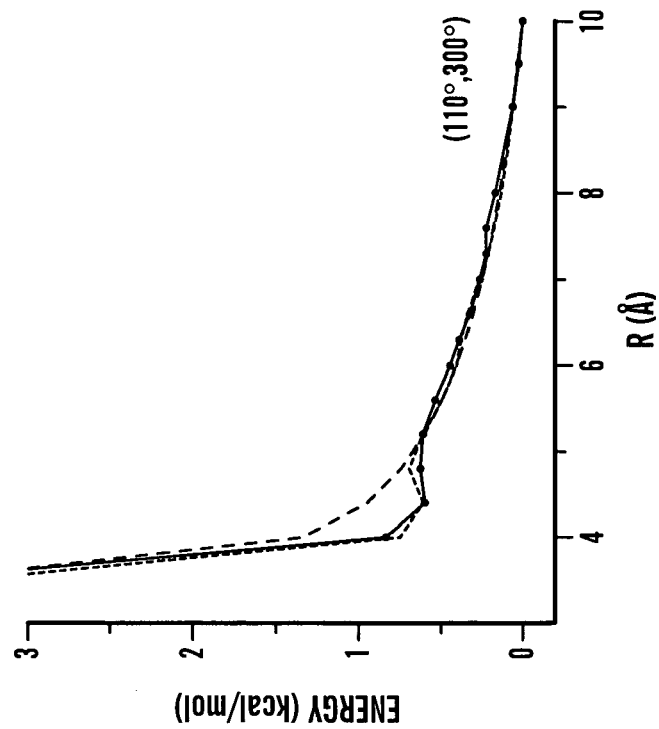
Figure 7C:
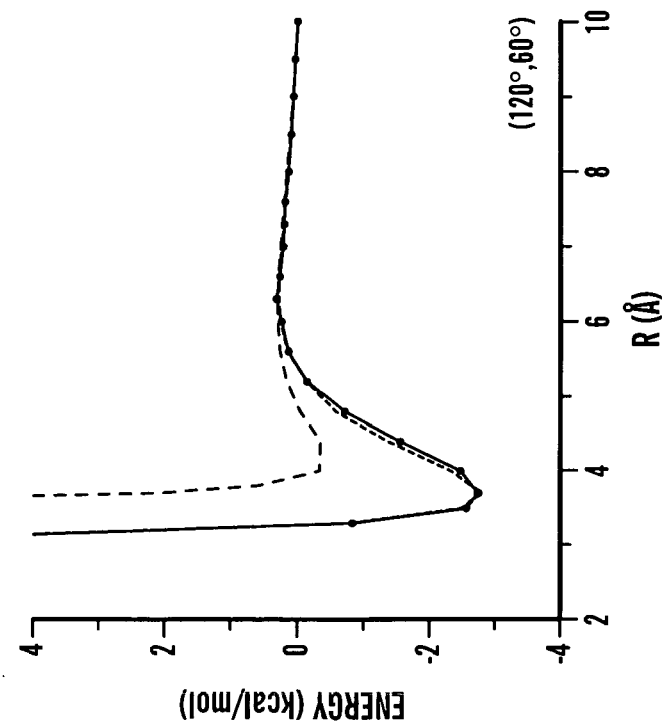
Figure 7F:
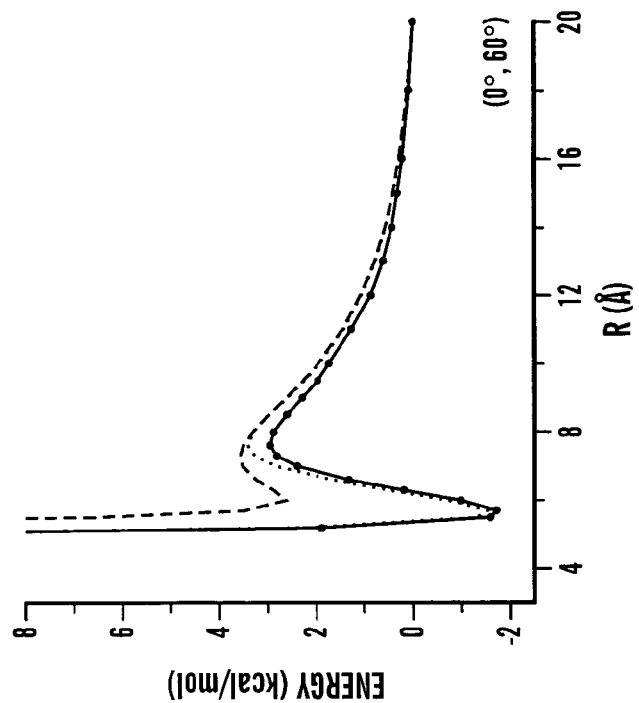
Figure 7E:
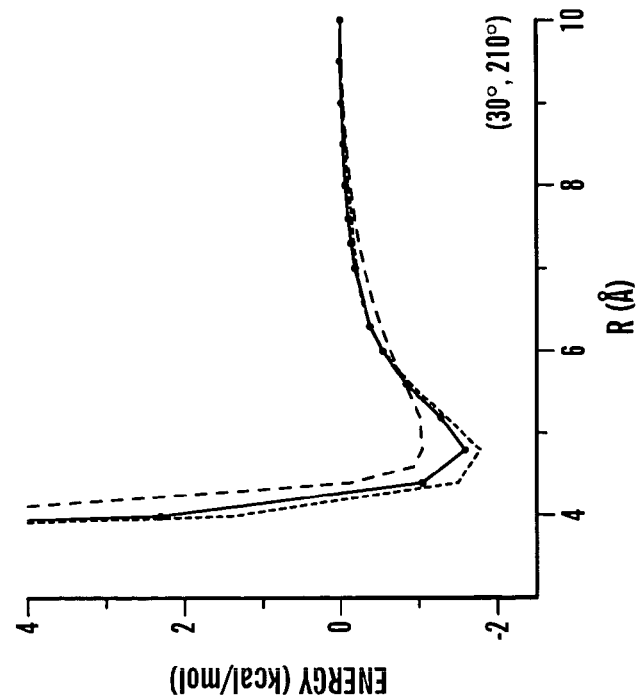
Figure 8A:
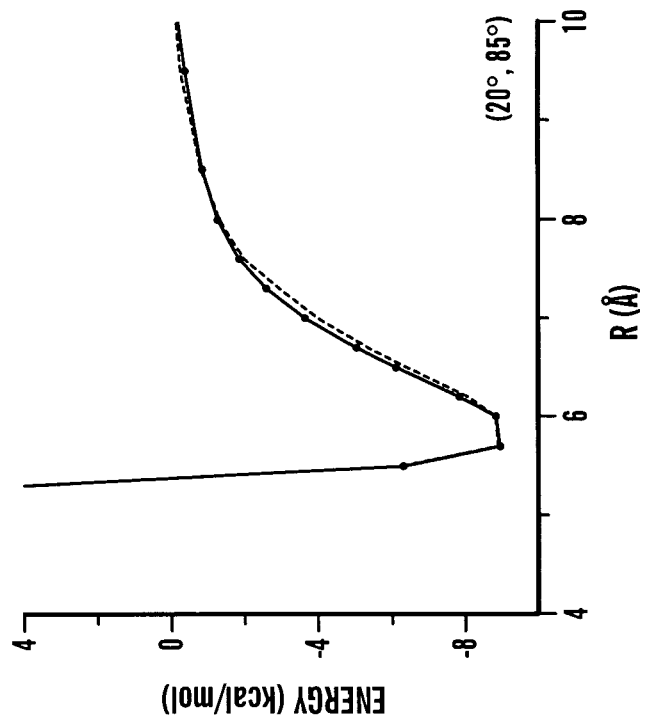
FIGS. 8A-8F represent 1D potential curves for Me-His-Ser-Me/water interaction at various directions obtained by MFCC and FS calculations using DFT B3LYP/6-31G. The solid line with dots are the FS result and the dotted lines are MFCC results.
Figure 8B:
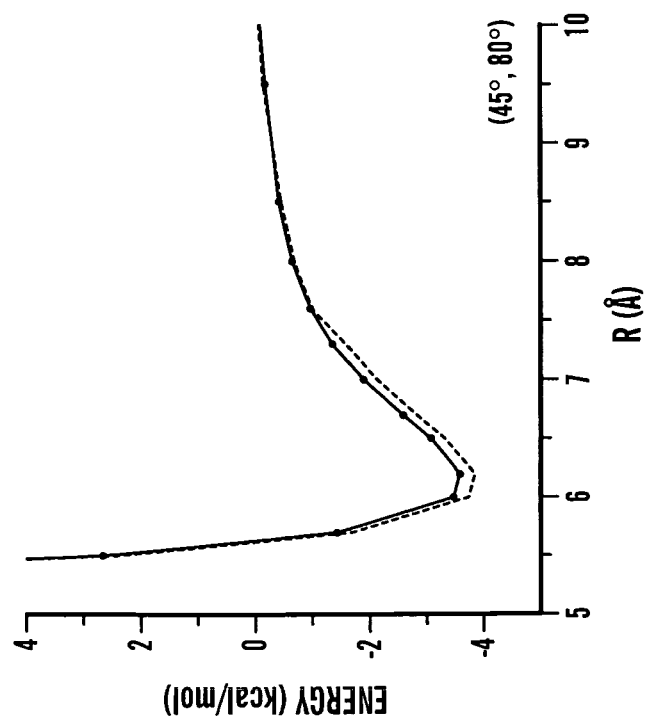
Figure 8D:
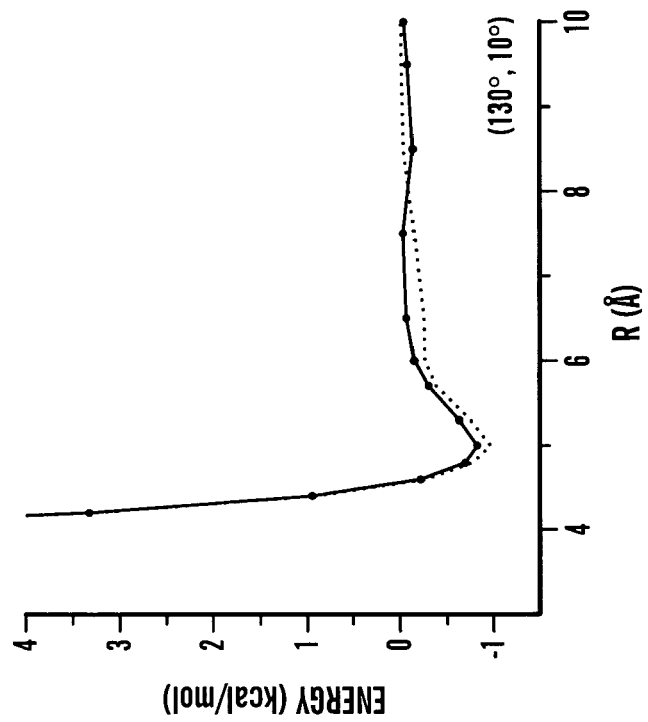
Figure 8C:
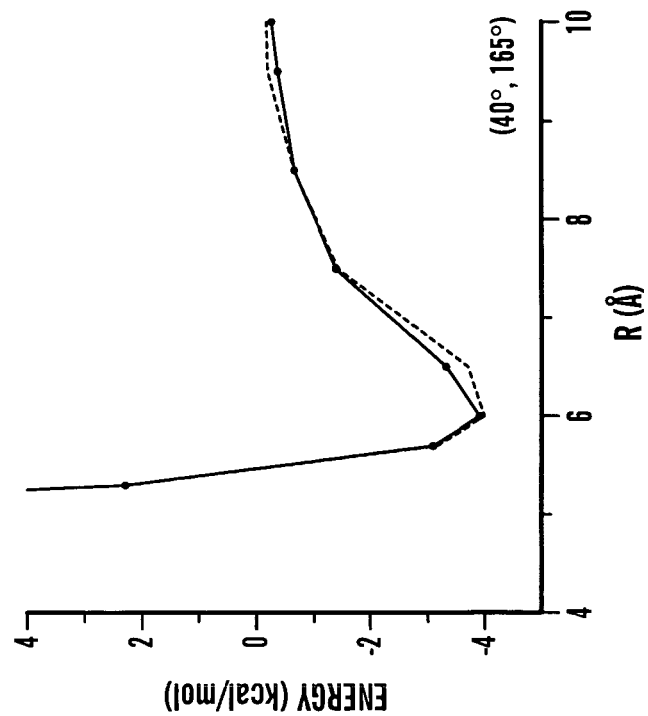
Figure 8F:
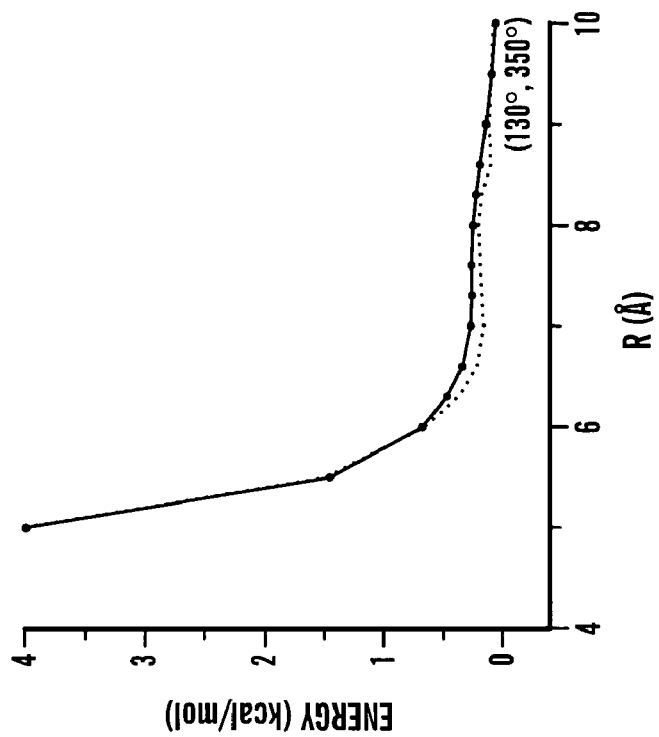
Figure 8E:
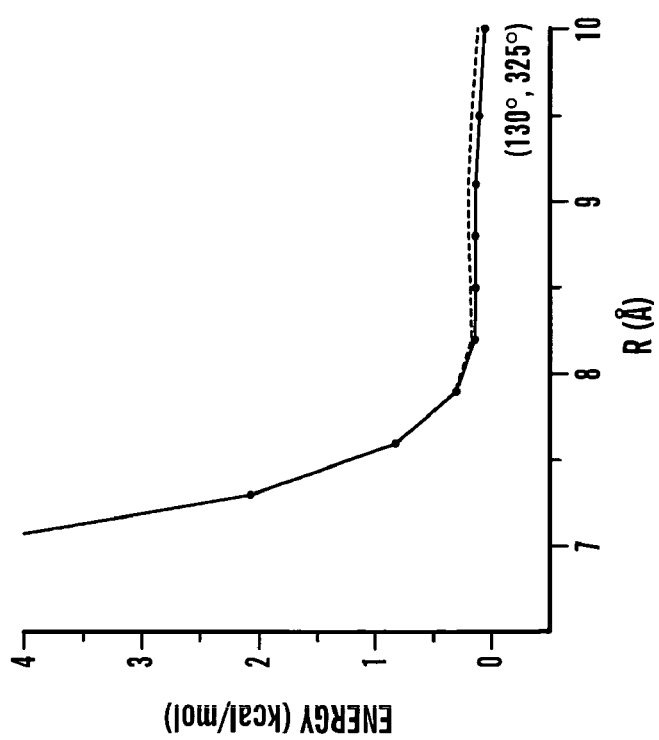
Figure 9A:
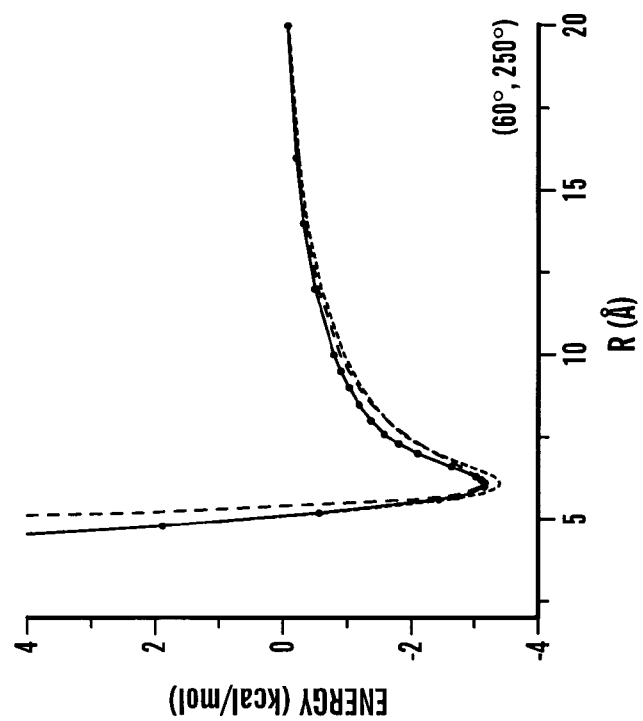
FIGS. 9A-9F represent 1D potential curves for Gly-Ser-Ala-Asp-Val/water interaction at various directions obtained by MFCC and FS calculations using HF/3-21G. The solid line with dots are the F result, the dotted lines are MFCC results, and the dashed lines are the results from AMBER force fields.
Figure 9B:
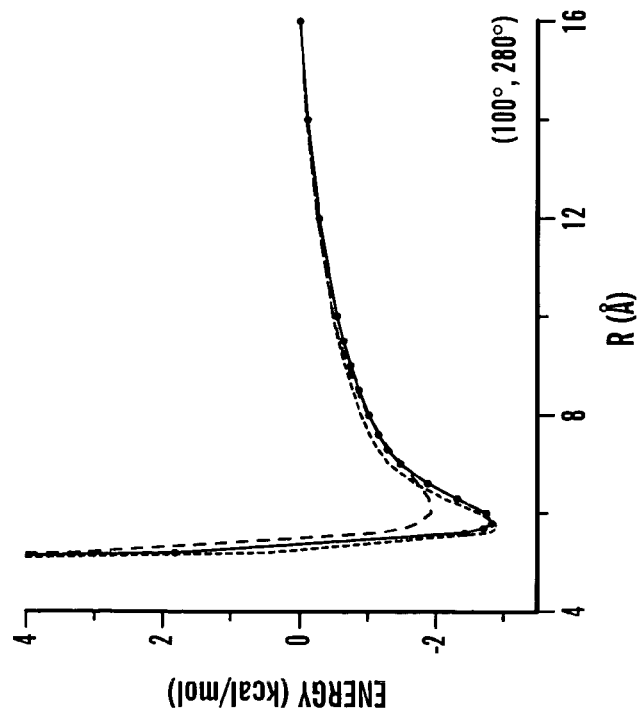
Figure 9D:
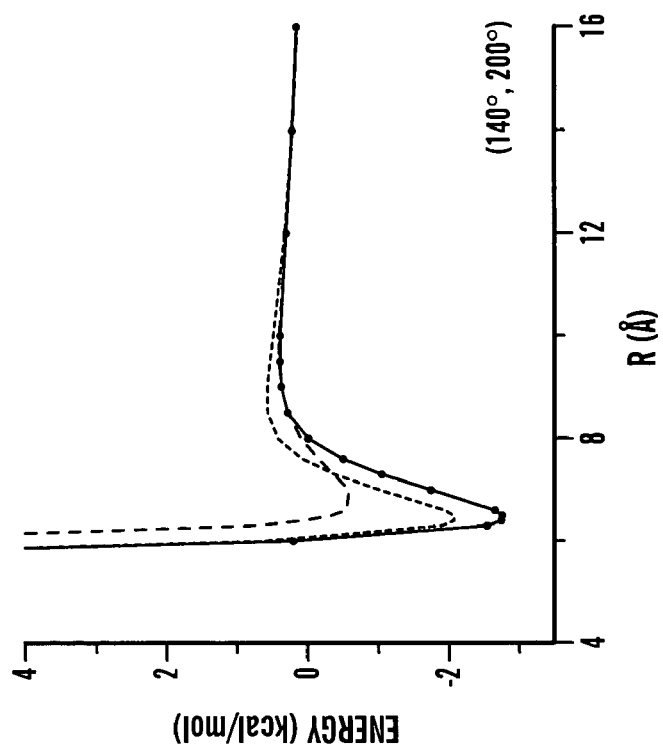
Figure 9C:
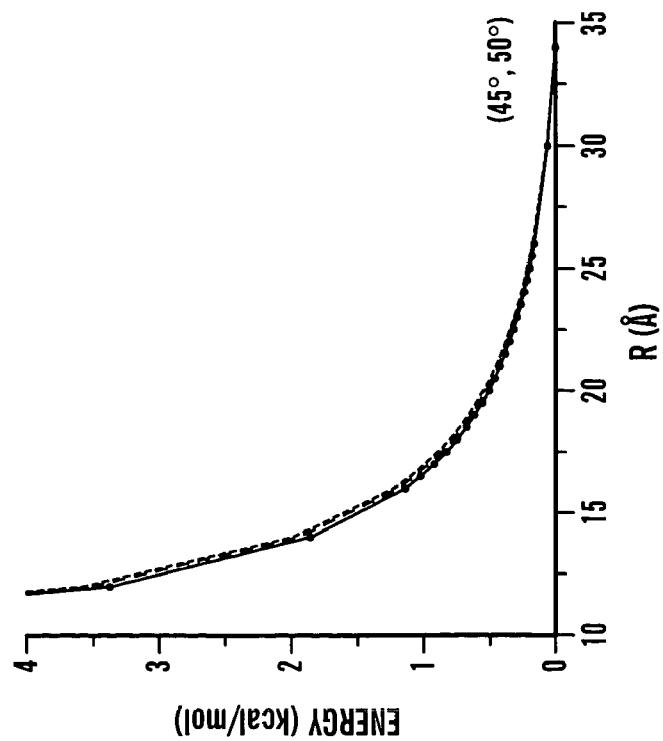
Figure 9F:
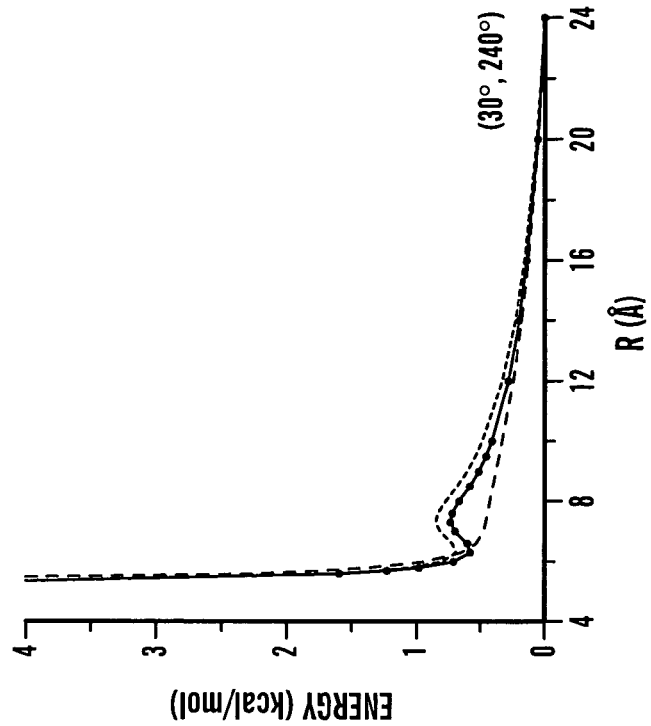
Figure 9E:
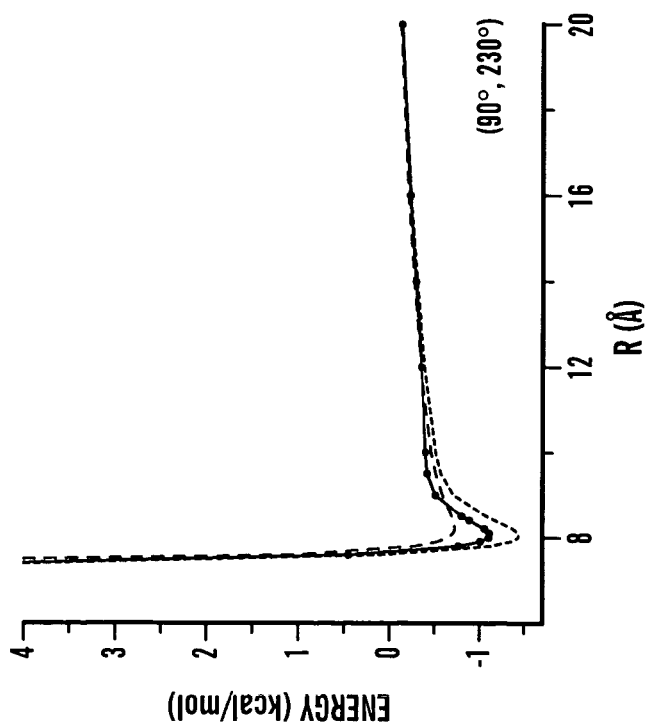
Figure 10B:
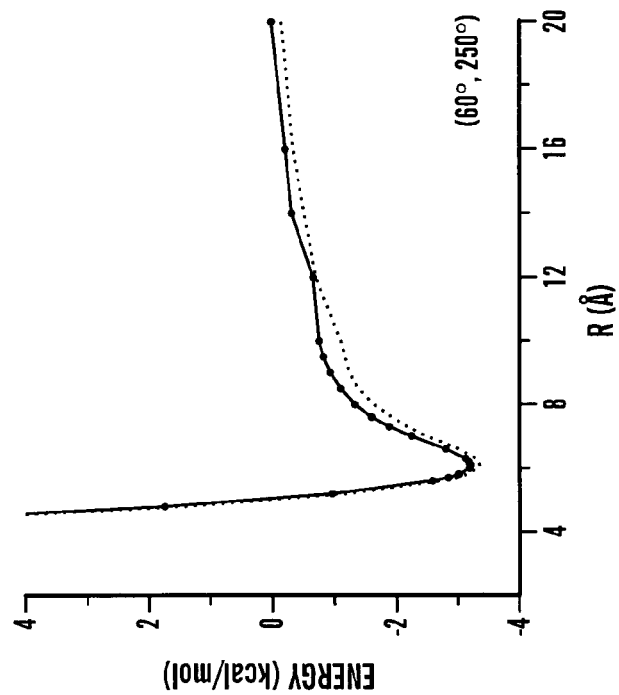
FIGS. 10A-10F represent 1D potential curves for Gly-Ser-Ala-Asp-Val/water interaction at various directions obtained by MFCC and FS calculations using DFT B3LYP/6-31G. The solid line with dots are the FS result and the dotted lines are MFCC results.
Figure 10A:
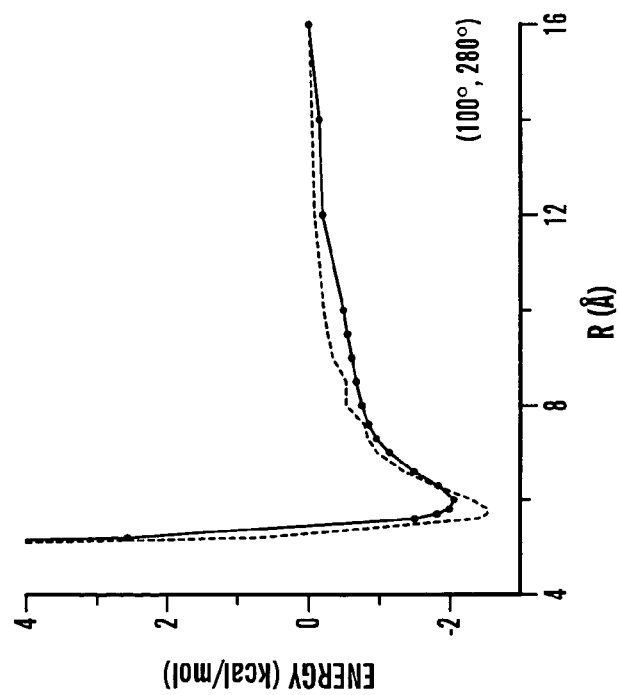
Figure 10D:
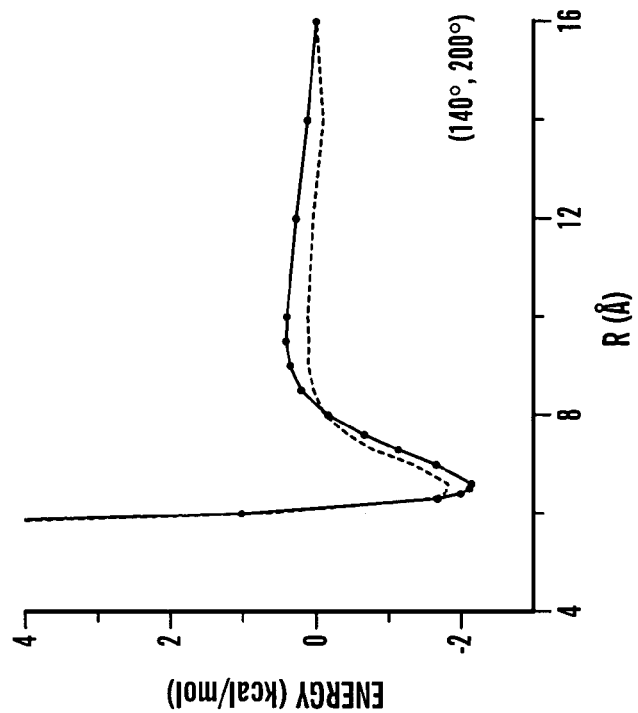
Figure 10C:
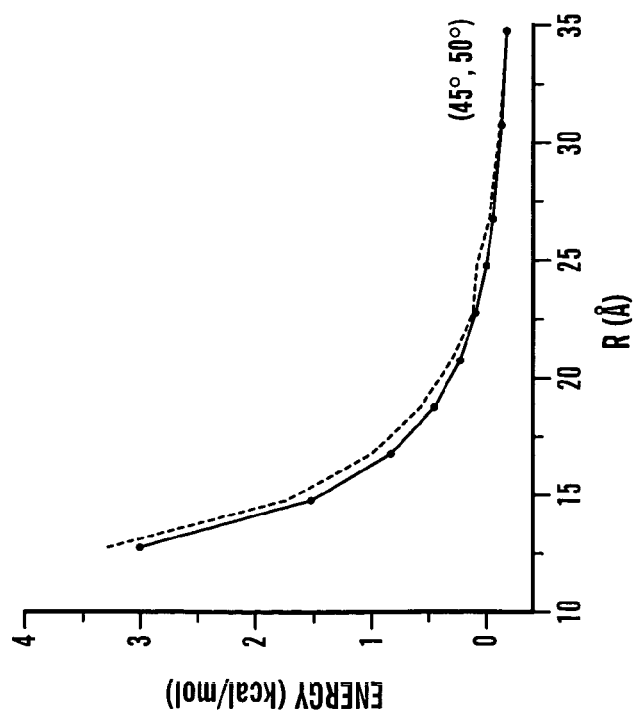
Figure 10F:
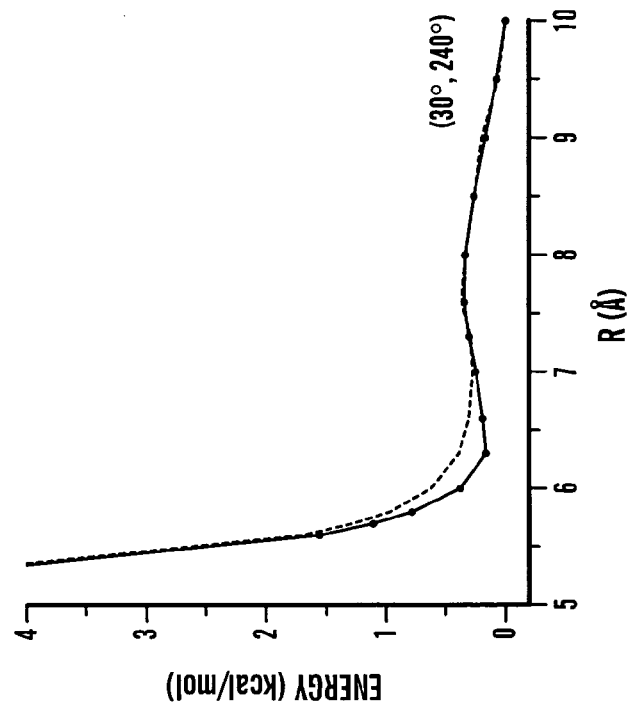
Figure 10E:
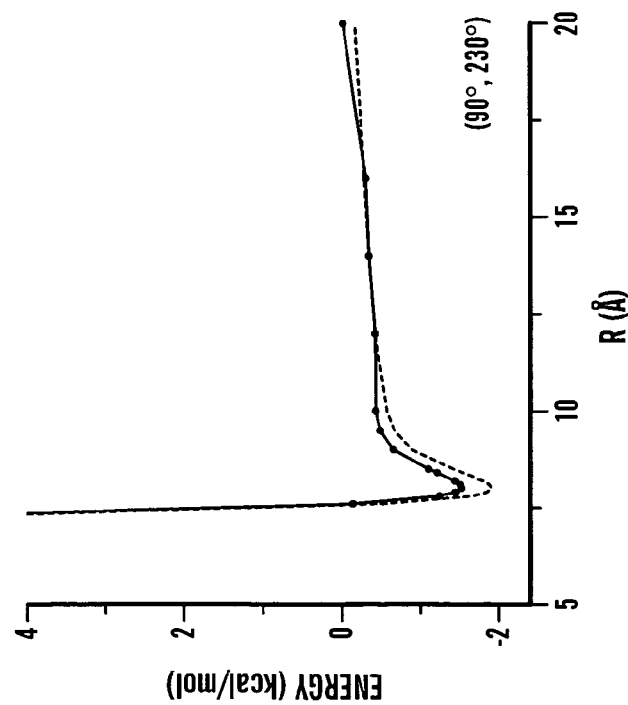

FIG. 6 shows ID potentials from ab initio calculations for the triglycine/water interaction in which the water molecule approaches the mass center of the peptide along the spherical angel (90, 0). In FIG. 6, the MFCC results calculated using HF and DFT methods with different basis sets were compared with the corresponding full system ab initio calculations. The results in FIG. 6 shows that although there are sizable differences among different ab initio calculations with different methods and different basis sets, the MFCC results are in excellent agreement with the corresponding FS calculations across the board. For example, the HF calculation with a 3-21G basis set gives a minimum energy which is about 5 kcal/mol lower than that calculated using a 6-31G basis set. The results from DFT/B3LYP calculations using 6-31G and 6-31G* are very close to each other and lie somewhere between two sets of HF calculations. However, in all four sets of calculations, the MFCC results are in excellent agreement with that from the corresponding FS calculations.

More results of calculations for the triglycine/water system at different geometries are shown in FIGS. 7A-F. Here the DFT B3LYP/6-31G method has been used for all ab initio calculations shown in FIGS. 7A-F in both MFCC and full system calculations. In all the six geometries with different approaching spherical angles of water toward peptide, the MFCC results are in excellent agreement with the full system calculations, both in structures and energies of the interaction potential. The largest errors between the MFCC and full system ab initio calculations are less than 0.5 kcal/mol in FIGS. 7A-F.

The interaction energies obtained from AMBER force fields for triglycine/water system at the same geometries are also shown in FIGS. 7A-F. As shown, the force field gives some reasonable minimum energy positions at these geometries. However, the force field does not give accurate energies. For example, in the potential curve with the spherical angle (90, 0) in FIGS. 7A-F, the minimum energy given by the force field is only about 7 kcal/mol compared to the ab initio energy of 13 kcal/mol. In another potential with the approaching angle of (120, 60) in FIGS. 7A-F, the well depth given by the force field is only about 0.3 kcal/mol compared to the ab initio calculation of 2.9 kcal/mol. Similar comparisons are seen for other potential curves in FIGS. 7A-F. Thus for the triglycine/water interaction, the force field generally gives energy minimums much higher than ab initio calculations.

For the second system of Me-His-Ser-Me in FIGS. 8A-F the dipeptide His-Ser has two methyl groups at the ends. The interaction potential energy curves are calculated for various approaching spherical angles of the water molecule toward the peptide. The comparison between the MFCC and full system calculations at B3LYP/6-31G level is given in FIGS. 8A-F. The results in FIGS. 8A-F show that both the structures and energies from the MFCC calculation are in excellent agreement with the results from the full system calculation. Even very shallow wells are accurately reproduced by the MFCC calculation. As shown in FIGS. 7A-F, the approaching angle of water at (130,10) exhibiting a well of less than 1 kcal/mol is accurately reproduced by the MFCC calculation. Both attractive and repulsive potentials are correctly reproduced by the MFCC calculation.

The third system tested is a relatively larger peptide with five amino acids having the sequence: Gly-Ser-Ala-Asp-Val (SEQ ID NO. 1) with charged terminals. This pentapeptide was specifically chosen to include all three types of side chains: the polar (Ser), nonpolar (Ala and Val) and charged (Asp) side chains and glycine (Gly). In addition, both the N- and C-terminals are charged. This pentapeptide/water system has a total number of 62 atoms. FIGS. 9A-F shows various 1D potential curves generated from ab initio calculations at the HF/3-21G level for different approaching angles of water. The agreement between the MFCC and full system ab initio calculations is generally very good for all potential curves as shown in FIGS. 9A-F. Both the structures of the potential curves and energies are quite well reproduced by MFCC calculations in all six cases. The largest deviation in energy from the full system calculation is about 0.5 kcal/mol in FIGS. 9A-F for the approaching angle of (140, 200). Even the structure of a small bump of about 0.4 kcal/mol for the water approaching angle (30, 240) is faithfully reproduced as shown in FIGS. 9A-F. For purpose of comparison, the potential curves obtained from the force field are also shown in FIGS. 9A-F. Similar to the results of the triglycine in FIGS. 7A-F, the force field generally gives too shallow wells relative to ab initio calculations. Next, the DFT calculations were performed at the B3LYP/6-31 G level for the same geometries of pentapeptide/water system; the results are shown in FIGS. 10A-F. Although there are differences in results between HF/3-21G and B3LYP/6-31G calculations, the MFCC calculation can reproduce the corresponding result of full system calculations using the same level of ab initio methods quite accurately as shown in FIGS. 10A-F.

FIGS. 11A-D shows positions of part of the gp41 atoms surrounding the water molecule shown with arrows. The structure of gp41 is obtained from PDB (protein data bank) and is fixed throughout the calculation. The ab initio calculation of the protein-water interaction is performed to generate 1D potential curves by moving the water molecule with fixed orientation along the direction indicated by the arrows as indicated in FIGS. 11A-D. Four different interaction paths were chosen as shown in FIGS. 11A-D. These paths generally involve some form of hydrogen bonding or attractive interactions. The one-dimensional distances are defined as the distance between the two atoms at both ends of the arrows except for FIG. 11A in which the distance is defined between the oxygen atom of water and the center-of-mass of the protein that lies along the direction of the arrow. The orientation of the water is fixed as it moves along the one-dimensional straight path to generate potential energies as a function of distance.

The ab initio calculation is performed using Gaussian98 package. Quantum chemistry calculations were performed at several levels of theory, i.e., HF, DFT/B3LYP and MP2. FIGS. 12A-D shows calculated 1D potential curves corresponding to the four different interaction paths illustrated in FIGS. 11A-D. For comparison, the corresponding potential curves generated from AMBER force field were plotted in FIGS. 12A-D. FIG. 12A shows the potential curve obtained by HF/3-21G calculation in which the x-coordinate is defined as the distance between the oxygen atom of the water and the center-of-mass of gp41 (shown in FIG. 11A). Comparison of the ab initio potential curve with that from the force field in FIG. 12A shows that there are apparent differences between the two potential curves. The minimum position given by the force field is shifted outward by about 0.3 Å in addition to some quantitative difference in energy scales. However, the HF/3-21G level of ab initio calculation employs a small basis size and include no electron correlation. While HF/3-21 G typically gives good equilibrium geometry, its calculated energy may not be very accurate, as is well known to those in the field.

TABLE 1

Figure 12A:
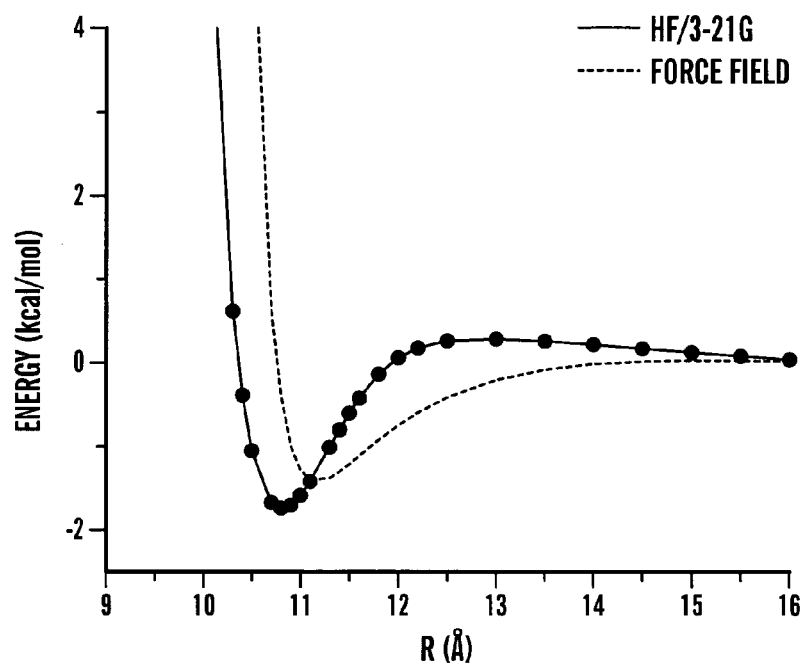
FIGS. 12A-12D represent the 1D (one-dimensional) gp41-water interaction potential curves as a function of interaction path defined in FIG. 9. The solid circles are the results of ab initio calculations and dotted lines are the results from AMBER force field. The B3LYP/6-31G and MP2/6-31G results are denoted, respectively, by open circles and open squares in (B) and (D).
Figure 12B:
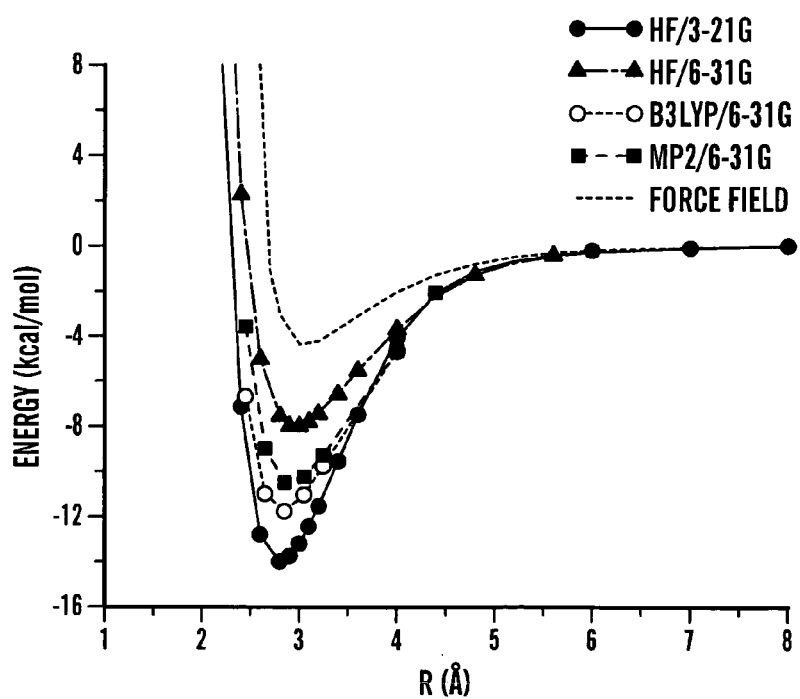
Figure 12C:
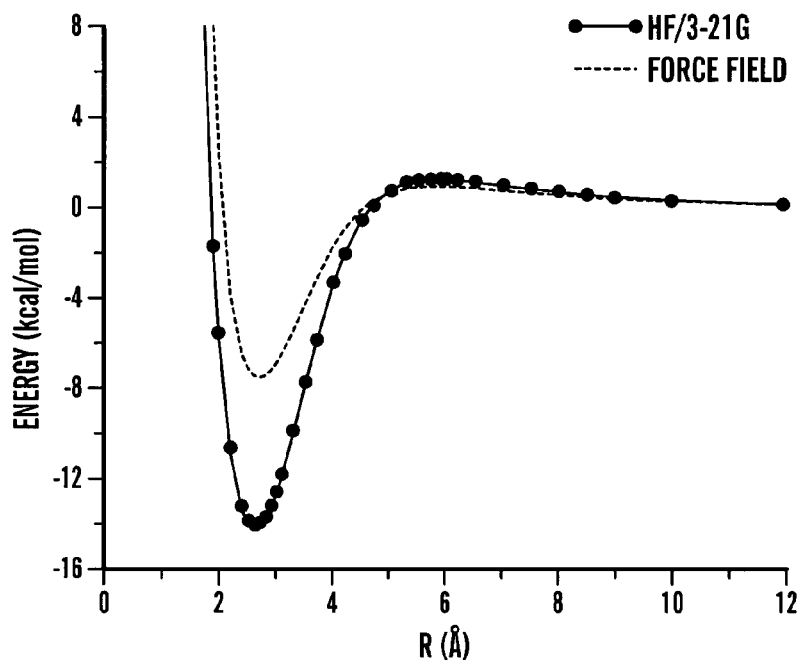
Figure 12D:
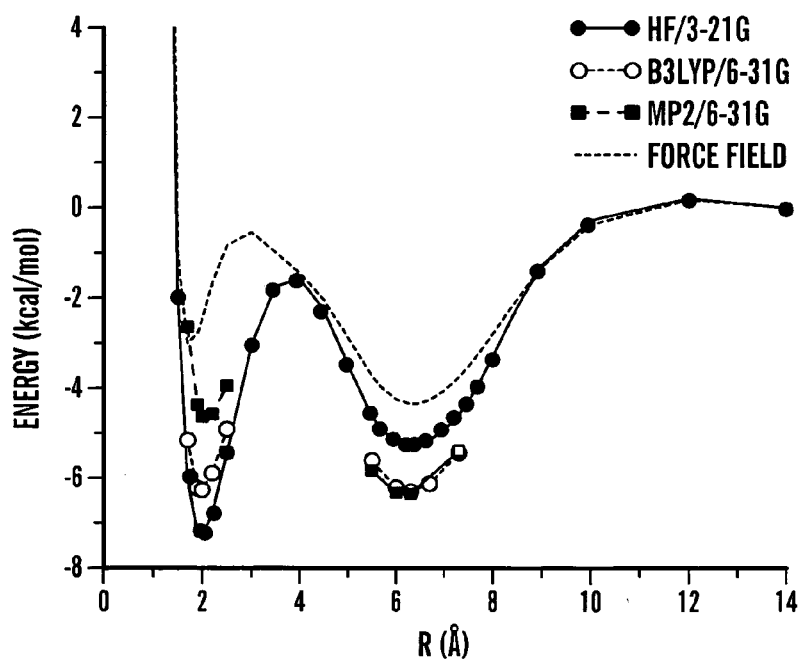

Calculated HIV-1 gp41-water interaction energies (kcal/mol) at minimum positions in FIG. 12B and FIG. 12D using different quantum chemistry methods as well as the AMBER force field.

| Methods | 2.85 Å[b] | 2.00 Å[d] | 6.30 Å[d] |
|---|---|---|---|
| Amber | −3.54 | −2.44 | −4.35 |
| HF/3-21G | −13.91 | −7.28 | −5.27 |
| HF/6-31G | −7.78 | | |
| B3LYP/6-31G | −11.77 | −6.27 | −6.31 |
| MP2/6-31G | −10.48 | −4.63 | −6.36 |

[b]Refers to the minimum position FIG. 12B.
[d]Refers to the minimum positions in FIG. 12D.

Figure 11A:
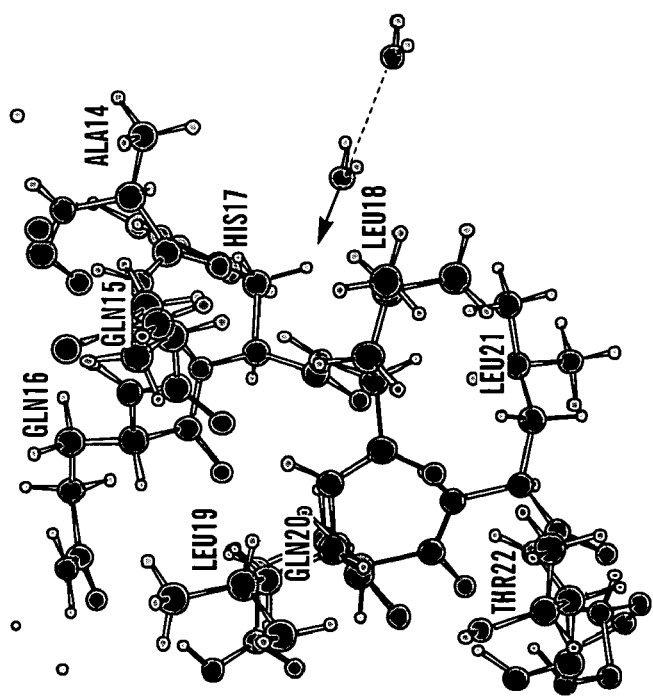
FIG. 11 represents illustrative interaction paths between a water molecule (indicated by arrows) and the fixed structure HIV-1 gp41 protein. The distances is defined between the two atoms on both ends of the arrows except for FIG. 11A where the distance is defined between the oxygen atom of the water and the center-of-mass of gp41.
Figure 11B:
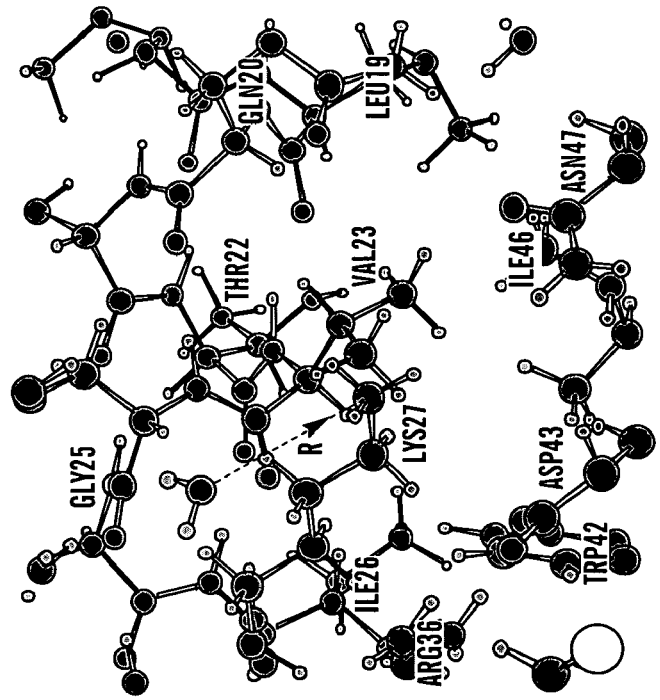

FIG. 12B shows another computed potential curve corresponding to the interaction path depicted in FIG. 11B. Here four different levels of calculations were employed: HF/3-21G, HF/6-31G, B3YLP/6-31G and MP2/6-31G. These calculations show that the HF/3-21G result gives rather accurate equilibrium positions but tends to overestimate the hydrogen bonding strength to some extent. In comparison, the HF/6-31G calculation gives bonding energy that seem to be too small. The more accurate calculation with B3LYP/6-31G, which includes electron correlation, gives bonding energy about 2 kcal/mol smaller than the HF/3-21G result and 4 kcal/mol larger than the HF/6-31G result (see Table 1). The MP2 calculation, also with 6-31G basis set, gives bonding energy about 1.3 kcal/mol smaller than the B3LYP energy. Based on conventional wisdom, the MP2 result is expected to be more reliable and trustworthy.

The force field gives good equilibrium position in FIG. 12B, but it gives bonding energy which is about 7 kcal/mol smaller than the MP2 energy. A similar result is seen in FIG. 12C corresponding to the interaction path shown in FIG. 11C. Here, the force field gives similar equilibrium position but underestimates the strength of hydrogen bonding, while the HF/3-21G is supposed to overestimate the bonding energy on the comparison in FIG. 12B.

Figure 11D:
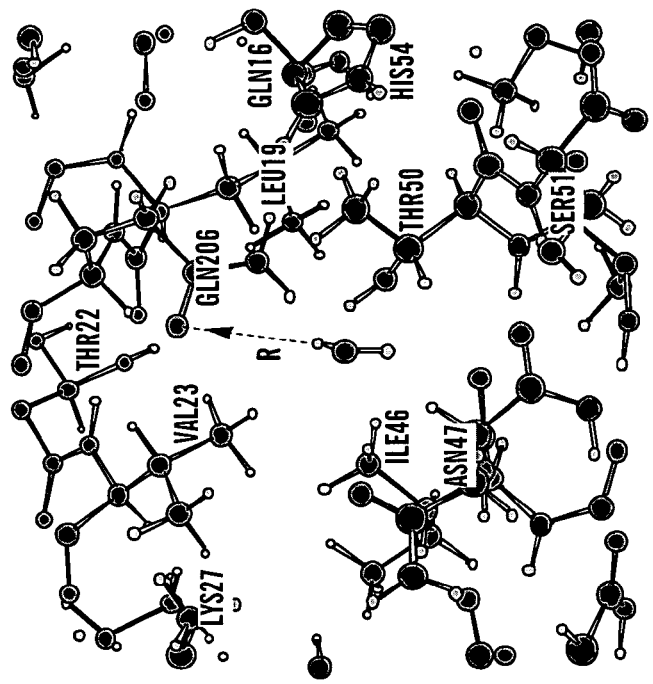
Figure 11C:
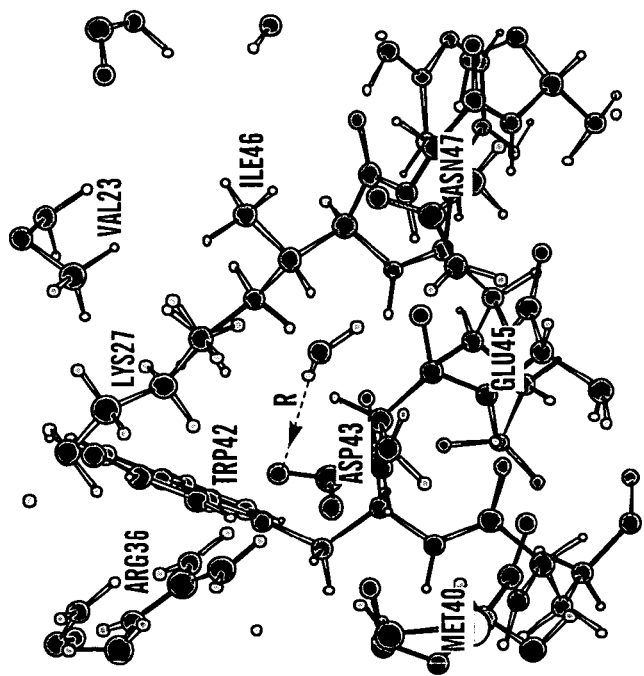

FIG. 12D shows the computed potential curve corresponding to the interaction path illustrated in FIG. 11D. As shown, this potential curve has two wells. The HF/3-21G calculation, while giving excellent positions of the wells, gives a inner well about 2 kcal/mol below the outer well (see Table 1). The B3LYP/6-31G calculation gives two well depths that are almost equal as can be seen in FIG. 12D and more clearly in Table 1. In comparison, the MP2/6-31G calculation, which is supposed to be more reliable, gives essentially the same well depth as the B3LYP calculation for the outer well. However, its calculated well depth for the inner well is about 1.6 kcal/mol above that of the B3LYP result as shown in Table 1 and in FIG. 12D. FIG. 12D also demonstrates that overall, the force field can qualitatively describe the interaction potential but not in a quantitative fashion.

The MFCC method is particularly suited for ab initio calculation of protein-drug interaction. Currently existing docking programs that play important roles in fast screening of drug candidates rely almost exclusively on empirical molecular force fields to obtain interaction energies. The MFCC method makes full quantum mechanical or ab initio calculation of targeted protein-inhibitor interaction possible and computationally practical. This could lead to a quantum jump in the understanding, prediction, and design of protein inhibitors in drug discovery and in other areas of chemical biology.

The computational cost is reduced using the MFCC method. In the numerical test, such as that performed in FIGS. 9A-F, a single point MFCC calculation using HF/3-21G method for the Gly-Ser-Ala-Asp-Val/water interaction system (with 62 atoms) takes about 2 minutes on a single processor Intel Pentium 1.5 GH linux workstation. In FIGS. 11A-D, a single-point energy calculation of the gp41-water interaction system (with 985 atoms) at the HF/3-21G level takes about 67 minutes on a Pentium 1.5 GH PC running linux. With respect to correlated methods, the corresponding single point calculation takes about 516 and 518 minutes, respectively, using B3LYP/6-31G and MP2/6-31G methods. In fact, the MP2 calculation does not take as much time as had been expected for large systems simply because each individual MP2 calculation involving a protein fragment is still relatively small despite the large size of the protein. This demonstrates that one could actually employ high level electron correlation methods to do practical calculations for protein-molecule interaction energies beyond HF and DFT methods.

Because the computational cost of the MFCC method is linearly proportional to the number of amino acids, the ab initio calculations may be extended straight to molecular interaction with real protein molecules with hundreds of amino acids. Thus the MFCC method makes full ab initio calculation of protein-molecular interaction energy practical even on personal computers. The ab initio calculation of the MFCC method can be easily parallelized to run on multi-node computer clusters in which individual fragments can be calculated simultaneously on separate computers. This can dramatically speed up the computation. For example, ab initio MFCC calculation for molecular interaction with a 200-residue protein on a 100-node clusters would take about the same amount of time as the that for molecular interaction with a 2-residue peptide on a single-node computer.

Full ab initio computation of interaction energies between a first molecule, such as a protein, and a second molecule, such as a water molecule, in which the entire system is included in the quantum mechanical treatment represents a new benchmark in extending quantum mechanical study to biological molecules.

The MFCC scheme is of particular relevance to the quantum mechanical calculations of protein-drug interactions. The process has been applied to the calculation for streptavidin-biotin binding complex and has been used to design a compound that shows better binding to HIV-1 RT than the FDA-approved drug Nevirapine.

What is claimed:

1. A computer-based method of calculating an intermolecular interaction energy between two molecules, comprising the steps of:
   providing a first molecule;
   decomposing the molecule into two or more molecular fragments;
   introducing one or more pairs of conjugate caps having a first cap member and a second cap member at each decomposition point of the molecular fragments to create a plurality of molecular portions, wherein each molecular portion comprises a fragment of the first molecule and at least one cap member;
   coupling each pair of conjugate caps to form one or more coupled caps;
   determining the interaction energies (a) between each molecular portion and a second molecule, and (b) between each pair of coupled caps and the second molecule;
   using a computer processor, calculating an intermolecular interaction energy between the first molecule and the second molecule based on the interaction energy determinations; and
   displaying the results of the calculated intermolecular interaction energy.

2. The method as set forth in claim 1, wherein the first molecule is provided by electronically generating a representation of a physical molecule.

3. The method as set forth in claim 2, wherein the decomposing step comprises electronically cutting the representation of the molecule.

4. The method as set forth in claim 3, wherein the introducing step comprises electronically introducing the one or more pairs of caps into the electronically generated first molecule.

5. The method as set forth in claim 1, wherein the step of determining interaction energy between the molecular portions and the second molecule comprises calculating an interaction energy between a first molecular portion and the second molecule on a first computing system, and calculating the interaction energy between a second molecular portion and the second molecule on a second computing system.

6. The method as set forth in claim 1, wherein the calculating step comprises
   summing together the interaction energies determined for each of the molecular portions and the second molecule to provide a total interaction energy of the molecular portions.

7. The method as set forth in claim 6, wherein the calculating step comprises
   summing together the conjugated cap interaction energies determined from each pair of coupled caps and the second molecule to provide a total conjugated cap interaction energy; and
   subtracting the total conjugated cap interaction energy from the total interaction energy of the molecular portions.

8. The method as set forth in claim 7, wherein the intermolecular interaction energy is a quantum mechanical intermolecular interaction energy.

9. The method as set forth in claim 1, wherein the first molecule is a polyatomic species.

10. The method as set forth in claim 9, wherein the polyatomic species is selected from the group consisting of, a protein, a peptide, a polymer, DNA, and RNA.

11. The method as set forth in claim 1, wherein the second molecule is selected from the group consisting of an ion, a water molecule, an inorganic molecule, an organic molecule, a drug molecule, and a biological molecule.

12. The method as set forth in claim 1, wherein the first molecule is a protein or a peptide and the second molecule is a drug molecule.

13. The method as set forth in claim 1, wherein the first and second cap members are independently selected from the group consisting of $NH_2$, HNCOH, $CH_3$, $CRH_2$, CRHCOH, $CRHCONH_2$, $CRHNH_2$, CRHNHCOH, COH, and $CONH_2$, wherein R is a carbon-containing group.

14. A non-transitory computer-readable storage medium having stored thereon computer-executable instructions for calculating an intermolecular interaction energy, said instructions comprising:
   computer-executable instructions for providing a first molecule;
   computer-executable instructions for decomposing the first molecule into two or more molecular fragments;
   computer-executable instructions for introducing one or more pairs of conjugate caps having a first cap member and a second cap member at each decomposition point of the molecular fragments to create a plurality of molecular portions, wherein each molecular portion comprises a fragment of the first molecule and at least one cap member;
   computer-executable instructions for coupling each pair of conjugate caps to form one or more coupled caps;
   computer-executable instructions for determining the interaction energies (a) between each molecular portion and a second molecule, and (b) between each pair of coupled caps and the second molecule;
   computer-executable instructions for calculating an intermolecular interaction energy between the first molecule and the second molecule based on the interaction energy determinations; and
   computer-executable instructions for displaying the results of the calculated intermolecular interaction energy;
   wherein the computer-readable medium is a physical medium.

15. The medium as set forth in claim 14, wherein the computer-executable instructions for calculating an intermolecular interaction energy comprise
   computer-executable instructions for summing together the interaction energies determined for each of the molecular portions and the second molecule to provide a total interaction energy of the molecular portions.

16. The medium as set forth in claim 15, wherein the computer-executable instructions for calculating an intermolecular interaction energy comprise
   computer-executable instructions for summing together the conjugated cap interaction energies determined from each pair of coupled caps and the second molecule to calculate a total conjugated cap interaction energy; and
   computer-executable instructions for subtracting the total conjugated cap interaction energy from the total interaction energy of the molecular portions to calculate the intermolecular interaction energy between the first molecule and the second molecule.

17. The medium as set forth in claim 16, wherein the intermolecular interaction energy is a quantum mechanical intermolecular interaction energy.

18. The medium as set forth in claim 14, wherein the first molecule is a polyatomic species.

19. The medium as set forth in claim 18, wherein the polyatomic species is selected from the group consisting of a material, a protein, a peptide, a polymer, DNA, and RNA.

20. The medium as set forth in claim 14, wherein the second molecule is selected from the group consisting of an ion, a water molecule, an inorganic molecule, an organic molecule, a drug molecule, and a biological molecule.

21. The medium as set forth in claim 14, wherein the first and second cap members are selected from the group consisting of $NH_2$, HNCOH, $CH_3$, $CRH_2$, CRHCOH, $CRHCONH_2$, $CRHNH_2$, CRHNHCOH, COH, and $CONH_2$, wherein R is a carbon-containing group.

22. A computer system for calculating an intermolecular interaction energy, the system comprising:
   a processor;
   a molecular generation module that provides a first molecule;
   a molecular decomposition module that decomposes the molecule into two or more molecular fragments; and
   a molecular cap introduction module that introduces one or more pairs of conjugate caps having a first cap member and a second cap member at each decomposition point of the molecular fragments to create a plurality of molecular portions, wherein each molecular portion comprises a fragment of the first molecule and at least one cap member;
   a coupling module that couples each pair of conjugate caps to form one or more coupled caps;
   an interaction energy module that determines the interaction energies (a) between each molecular portion and a second molecule, and (b) between each pair of coupled caps and the second molecule;
   an intermolecular interaction energy module that calculates an intermolecular interaction energy between the first molecule and the second molecule based on the interaction energy determinations; and
   a displaying module that displays the results of the calculated intermolecular interaction energy.

23. The system as set forth in claim 22, wherein the interaction energy module comprises at least one first computing system that determines an interaction energy between a first molecular portion and the second molecule, and at least one second computing system that determines an interaction energy between a second molecular portion and the second molecule.

24. The system as set forth in claim 22, wherein the intermolecular interaction energy module sums together the interaction energies determined for each of the molecular portions and the second molecule to provide a total interaction energy of the molecular portions.

25. The system as set forth in claim 24, wherein the intermolecular interaction energy module
   sums together the conjugated cap interaction energies determined from each pair of coupled caps and the second molecule to provide a total conjugated cap interaction energy; and
   subtracts the total conjugated cap interaction energy from the total interaction energy of the molecular portions to calculate the intermolecular interaction energy between the first molecule and the second molecule.

26. The system as set forth in claim 25, wherein the intermolecular interaction energy is a quantum mechanical intermolecular interaction energy.

27. The system as set forth in claim 22, wherein the first molecule is a polyatomic species.

28. The system as set forth in claim 27, wherein the polyatomic species is selected from the group consisting of, a protein, a peptide, a polymer, DNA, and RNA.

29. The system as set forth in claim 22, wherein the second molecule is selected from the group consisting of an ion, a water molecule, an inorganic molecule, an organic molecule, a drug molecule, and a biological molecule.

30. The system as set forth in claim 22, wherein the first molecule is a protein or a peptide and the second molecule is water.

31. The system as set forth in claim 22, wherein the first and second cap members are selected from the group consisting of $NH_2$, HNCOH, $CH_3$, $CRH_2$, CRHCOH, $CRHCONH_2$, $CRHNH_2$, CRHNHCOH, COH, and $CONH_2$, wherein R is a carbon-containing group.

* * * * *